US006642048B2

(12) United States Patent
Xu et al.

(10) Patent No.: US 6,642,048 B2
(45) Date of Patent: Nov. 4, 2003

(54) CONDITIONED MEDIA FOR PROPAGATING HUMAN PLURIPOTENT STEM CELLS

(75) Inventors: Chunhui Xu, Cupertino, CA (US); Joseph D. Gold, San Francisco, CA (US)

(73) Assignee: Geron Corporation, Menlo Park, CA (US)

( * ) Notice: Subject to any disclaimer, the term of this patent is extended or adjusted under 35 U.S.C. 154(b) by 26 days.

(21) Appl. No.: 09/900,752

(22) Filed: Jul. 6, 2001

(65) Prior Publication Data

US 2002/0022268 A1 Feb. 21, 2002

Related U.S. Application Data

(60) Provisional application No. 60/216,387, filed on Jul. 7, 2000, and provisional application No. 60/220,064, filed on Jul. 21, 2000.

(51) Int. Cl.$^7$ ............................. C12N 5/08; C12N 5/00; C12N 5/02; C12N 5/06; C12N 5/10
(52) U.S. Cl. ....................... 435/366; 435/325; 435/374; 435/363; 435/383; 435/384
(58) Field of Search ................................ 435/325, 363, 435/366, 377, 374, 383, 384

(56) References Cited

U.S. PATENT DOCUMENTS

| | | | |
|---|---|---|---|
| 4,423,145 A | 12/1983 | Stampfer et al. ............. 435/32 |
| 5,166,065 A | 11/1992 | Williams .................. 435/240.1 |
| 5,362,642 A | 11/1994 | Kern ........................ 435/240.1 |
| 5,405,772 A | 4/1995 | Ponting ................. 435/240.31 |
| 5,453,357 A | 9/1995 | Hogan ........................ 435/7.21 |
| 5,523,226 A | 6/1996 | Wheeler ................... 435/240.2 |
| 5,635,387 A | 6/1997 | Fei et al. ..................... 435/378 |
| 5,843,780 A | 12/1998 | Thomson .................... 435/363 |
| 5,914,268 A | 6/1999 | Keller et al. ................ 435/325 |
| 5,922,597 A | 7/1999 | Verfaillie et al. ......... 435/372.1 |
| 5,942,435 A | 8/1999 | Wheeler ..................... 435/325 |
| 5,994,129 A | 11/1999 | Armstrong et al. .......... 435/325 |
| 6,022,742 A | 2/2000 | Kopf .......................... 435/383 |
| 6,245,566 B1 | 6/2001 | Gearhart et al. ............. 435/384 |
| 6,261,556 B1 | 7/2001 | Weinrich et al. ........... 424/94.5 |
| 6,372,494 B1 | 4/2002 | Naughton et al. .......... 435/391 |

FOREIGN PATENT DOCUMENTS

| | | |
|---|---|---|
| WO | WO 97/21802 | 12/1995 |
| WO | WO 96/17627 | 6/1996 |
| WO | WO 97/30151 | 8/1997 |
| WO | WO 97/47734 | 12/1997 |
| WO | WO 98/30679 | 7/1998 |
| WO | WO 99/20741 | 4/1999 |
| WO | WO 99/42122 | 8/1999 |

OTHER PUBLICATIONS

Thomson et al. PNAS, 92:7844–7848, 1995.*
Amit, et al., Clonally Derived Human Embryonic Stem Cell Lines Maintain Pluripotency and Proliferative Potential for Prolonged Peroids of Culture, Dev. Biol. 227–271 (2000).
Baribault et al., Embryonic Stem Cell Culure an dGene Targeting in Transgenic Mice, Mol. Biol. Med 6:481 (1989).
Berger et al., Self Renewal of Embryonic Stem Cells in the Absence of Feeder Cells and Exogenous Leukaemia Inhibitory Factor, Growth Factors 14:154 (1997).
Bodnar et al., Extension of Life–Span by Introduction of Telomerase into Normal Human Cells, Science 279:349 (1988).
Bongso et al., Improved Quality of Human Embryos when co–cultured with Human Ampullary Cells, Hum. Reprod. 4:706 (1989).
Evans et al., Establishment in Culture of Pluripotential Cell from Mouse Embryos, Nature 292:154 (1981).
Gardner et al., Clture and Transfer of Human Blastocysts Increases Implantation Rates and Reduces the Need for Multiple Embryo Transfers, Fertil. Steril. 69:84 (1998).
Gendall et al., Isolation and Characterization of a Leukaemia Inhibitory Factor–Independent Embryonic Stem Cell Line, int, J. Biochem. Cell Biol. 29:829 (1997).
Matsui et al., Derivation of Pluripotential Embryonic Stem Cells from Murine Primordial Germ Cells in Culture, Cell 70:841 (1992).
Nichols et al., Dervation of Germline Competent Embroyonic Stem Cells with a Combination of Interleukin–6 and Soluble Interleukin–6 Receptor, Exp. Cell Res. 215:237 (1994).
Nichols et al., Establishment of Germ–Line–Competent Embryonic Stem (ES) Cells Using Differetiation Inhibiting Activity, Development 110:1341 (1990).

(List continued on next page.)

*Primary Examiner*—Deborah Crouch
*Assistant Examiner*—Thai-An N. Ton
(74) *Attorney, Agent, or Firm*—J Michael Schiff; David J. Earp

(57) ABSTRACT

This invention provides media that support the growth of primate pluripotent stem cells in feeder-free culture, and cell lines useful for producing such media and other purposes. Conventionally, it has been necessary to grow pluripotent embryonic cells on feeder layers of primary embryonic fibroblasts, in order to prevent them from differentiating. It has now been discovered that standard culture media conditioned by special cell lines can be used to support proliferation of pluripotent stem cells while inhibiting differentiation in an environment free of feeder cells. This invention includes mesenchymal and fibroblast-like cell lines obtained from embryonic tissue or differentiated from embryonic stem cells. Methods for deriving such cell lines, processing media, and growing stem cells using the conditioned media are described and illustrated in this disclosure.

35 Claims, 11 Drawing Sheets

OTHER PUBLICATIONS

Figure 1C:
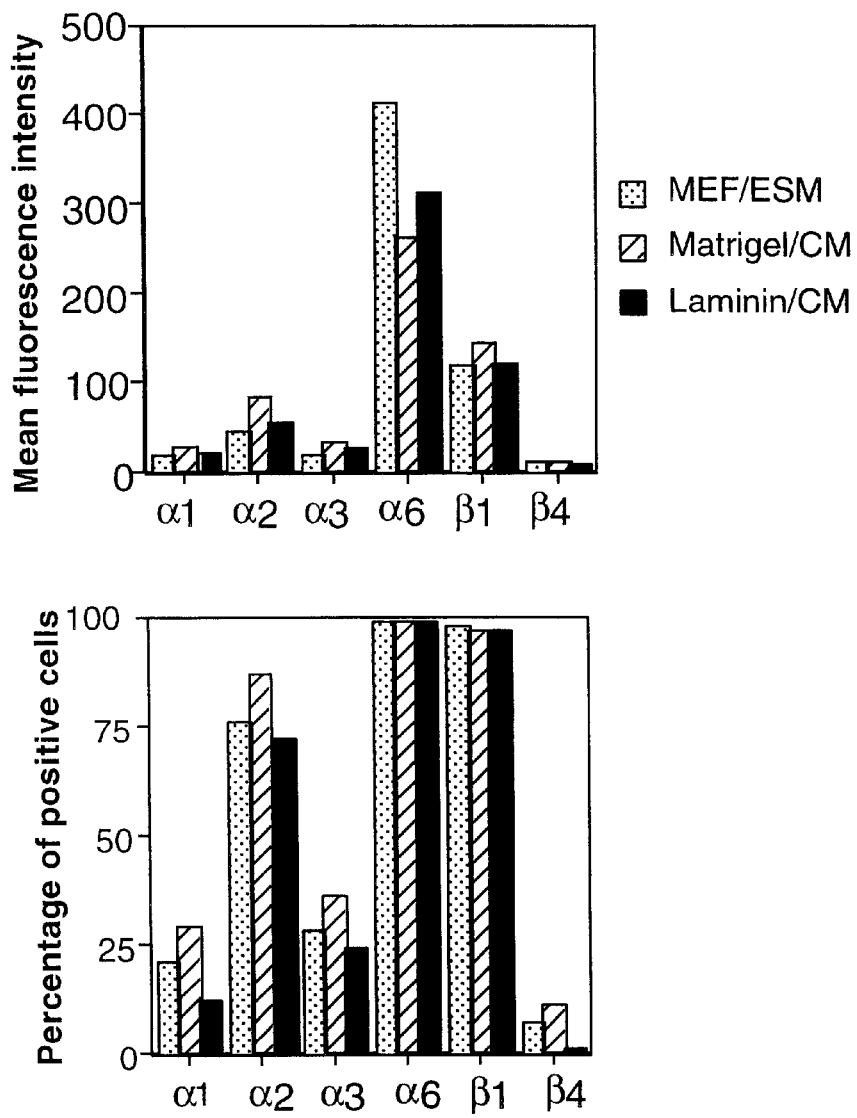

O'Shea., Embryonic Stem Cell Models of Development, New Anat. 257:32 (1999).

Pease et al., Isolation of Embryonic Stem (ES) Cells in Media Supplemented with Recombinant Leukaemia Inhibitory Factor (LIF), Developmental Biol. 141:344 (1990).

Pedersen., Studies of In Vitro Differentiation with Embryonic Stem Cells, Reprod. Fertil. Dev. 6:543 (1994).

Robertson., Derivation and Maintenance of Embroyonic Stem Cell Cultures, Methods in Mol. Bio. 75:173 (1997).

Rose et al., Oncostatin M (OSM) Inhibits the Differentiation of Pluripotent Embryonic Stem Cells In Vitro, Cytokine 6:48 (1994).

Shamblott et al., Derivation of Pluripotential Stem Cells from Cultured Human Primordial Germ Cells, Proc. Natl. Acad. Sci. USA 95:13726 (1998).

Smith et al., Inhibition of Pluripotential Embryonic Stem Cell Differentiation by Purifed Polypeptides, Nature 366:668 (1998).

Thomson et al., Embroyonic Stem Cell Lines Derived from Human Blastocysts, Science 282:1145 (1998).

Thomson et al., Primate Embryonic Stem Cells, Current Topics in Developmental Biol. 38:133 (1998).

* cited by examiner

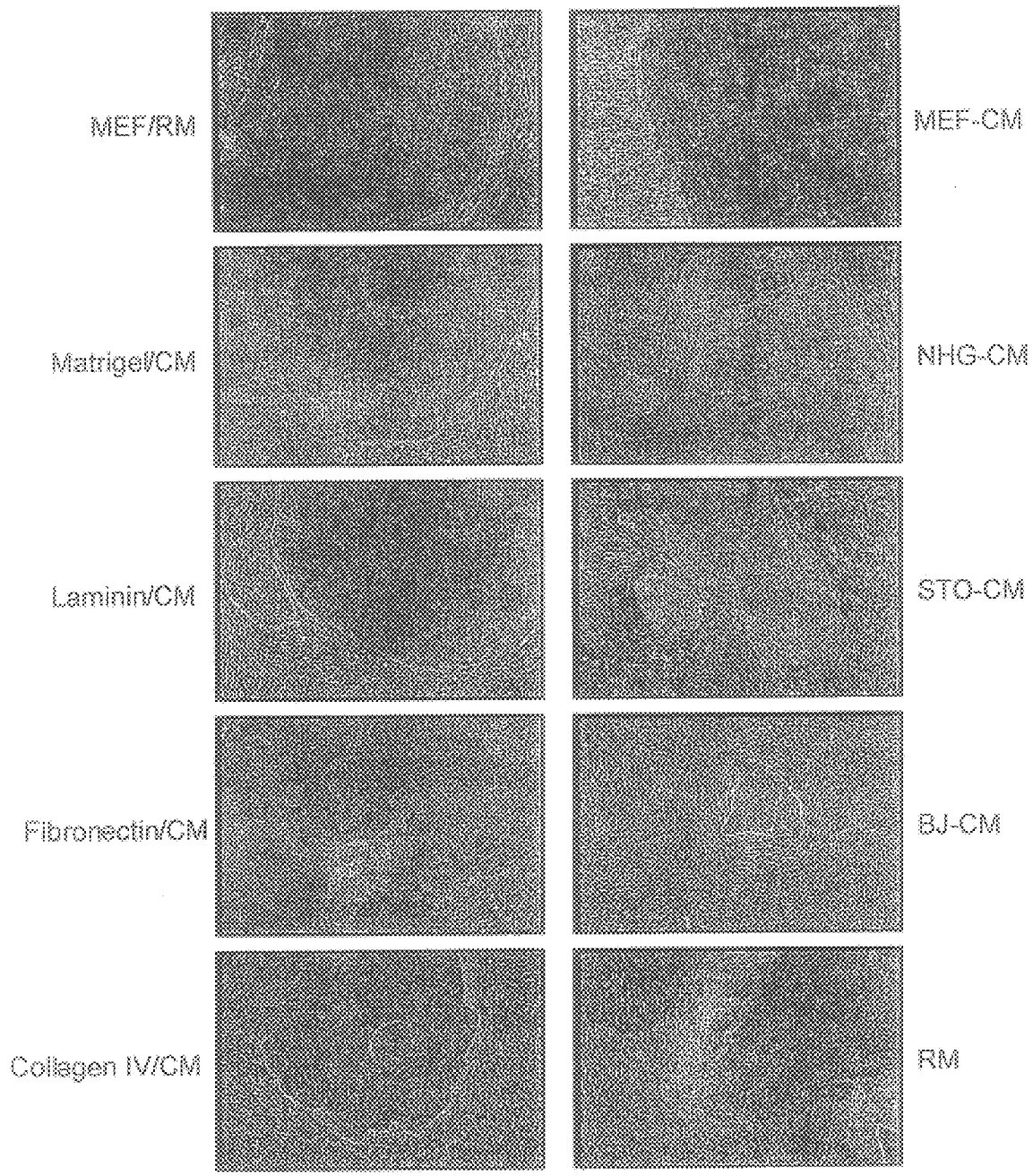

HEF1–hTERT

HEF1–control

CONDITIONED MEDIA FOR PROPAGATING HUMAN PLURIPOTENT STEM CELLS

RELATED APPLICATIONS

This application claims priority to pending U.S. provisional patent applications 60/216,387, filed Jul. 7, 2000; and 60/220,064, filed Jul. 21, 2000.

The aforelisted priority applications are hereby incorporated herein by reference in their entirety, as are the following: U.S. Ser. No. 60/175,581, filed Jan. 11, 2000; U.S. Ser. No. 09/688,031, filed Oct. 10, 2000; U.S. Ser. No. 09/718,308, filed Nov. 20, 2000; and International Patent Application PCT/US01/01030, filed Jan. 10, 2001.

TECHNICAL FIELD

This invention relates generally to the field of cell biology of embryonic cells. More specifically, it relates to the derivation of cell lines producing conditioned culture media, which in turn can be used to propagate human pluripotent stem cells in feeder-free culture.

BACKGROUND

A number of recent discoveries have raised expectations that stem cells may be a source of replacement cells and tissue for cells and tissues that are damaged in the course of disease, infection, or because of congenital abnormalities. Various types of putative stem cells differentiate when they divide, maturing into cells that can carry out the unique functions of particular tissues, such as the heart, the liver, or the brain.

A particularly important discovery has been the development of human pluripotent stem (hPS) cells (reviewed by R. A. Pedersen, Scientif. Am. 280(4):68, 1999). These cells have the capacity to differentiate into essentially all types of cells in the body. For example, hPS cells have been used to generate cells that are committed to a number of different cell lineages, which retain their capacity to proliferate. Since these embryonic cells are truly pluripotent, they have the potential to provide a stock supply of different types of cells for regeneration of essentially any type of failed tissue.

Early work on embryonic stem cells was done in mice (reviewed in Robertson, Meth. Cell Biol. 75:173, 1997; and Pedersen, Reprod. Fertil. Dev. 6:543, 1994). Desirable characteristics of stem cells are that they be capable of indefinite proliferation in vitro in an undifferentiated state, retain a normal karyotype, and retain the potential to differentiate to derivatives of all three embryonic germ layers (endoderm, mesoderm, and ectoderm).

The usual method for culturing mouse stem cells is to grow them on a layer of embryonic fibroblast feeder cells, such as the STO cell line. Cells from a previous culture are dispersed into a single cell suspension and cultured on the feeder cell layer. In some experimental procedures, it is possible to grow the mouse stem cells on gelatin plates without feeder cells, using recombinant soluble leukemia inhibitory factor (LIF) to replace the activity normally provided by the STO feeder cells (Robertson, supra). The presence of LIF is sufficient to keep the mouse stem cells from differentiating. By continuous passage of mouse stem cells, Berger et al. (Growth Factors 14:145,1997) selected out several cell lines independent of exogenously added LIF.

The morphology, cell surface markers, and growth requirements of embryonic cells from other species differ significantly from mouse embryonic stem cells. Stem cells from primate embryos are fragile, and it has been difficult to determine conditions that allow them to grow in culture. Thomson et al. (U.S. Pat. No. 5,843,780; Proc. Natl. Acad. Sci. U.S.A. 92:7844, 1995) were the first to successfully culture stem cells from primates. They subsequently derived human embryonic stem (hES) cell lines from human blastocysts (Science 282:114, 1998). Gearhart and coworkers derived human embryonic germ (hEG) cell lines from fetal gonadal tissue (Shamblott et al., Proc. Natl. Acad. Sci. U.S.A. 95:13726, 1998 and International Patent Publication WO 98/43679). Both hES and hEG cells have the long-sought characteristics of hPS cells: they are capable of long-term proliferation in vitro without differentiating, they retain a normal karyotype, and they retain the capacity to differentiate to a number of different derivatives.

A major obstacle to the use of such cells in human therapy is that the originally described methods to propagate them involved culturing on a layer of feeder cells. For example, when cultured in a standard culture environment in the absence of mouse embryonic fibroblasts as feeder cells, the hPS cells rapidly differentiate or fail to survive. Unlike mouse ES cells, the presence of exogenously added LIF does not prevent differentiation of the human ES cells. Unfortunately, the use of feeder cells substantially increases the cost of production, and makes scale-up of hPS cell culture impractical. The feeder cells are metabolically inactivated to keep them from outgrowing the stem cells, so it is necessary to have fresh feeder cells for each splitting of the hES culture. Furthermore, procedures are not yet developed for completely separating feeder cell components away from embryonic cells prepared in bulk culture. When embryonic cells are grown using currently available culture methods, the presence of xenogeneic components from the feeder cells complicates their potential use in human therapy.

International Patent Publication WO/9920741 (Geron Corp.) is entitled "Methods and Materials for the Growth of Primate-Derived Primordial Stem Cells". In one embodiment, a cell culture medium is provided for growing primate-derived primordial stem cells in a substantially undifferentiated state, having a low osmotic pressure and low endotoxin levels. The basic medium is combined with a nutrient serum effective to support the growth of primate-derived primordial stem cells and a substrate of feeder cells or an extracellular matrix component derived from feeder cells. The medium further includes non-essential amino acids, an anti-oxidant, and growth factors that are either nucleosides or a pyruvate salt.

New technology to facilitate growing undifferentiated hPS cells without feeders would be a major achievement towards realizing the full potential of embryonic cell therapy. In particular, there is a need for media that support feeder-free culture that is compatible with regulatory requirements for human administration, and can be scaled up for commercial production.

SUMMARY

This invention provides media that support the growth of primate pluripotent stem (pPS) cells in feeder-free culture, and cell lines useful for production of such media.

One embodiment of this invention is a method for preparing a conditioned medium suitable for culturing pPS cells in a growth environment essentially free of feeder cells, comprising conditioning medium by culturing cells in the medium, and then harvesting the conditioned medium.

Another embodiment of this invention is a method for culturing pPS cells, comprising providing a conditioned medium of this invention, and culturing pPS cells in a feeder-free growth environment containing the conditioned medium. In either of these embodiments, the pPS cells can be human embryonic stem (hES) cells.

The cells used for conditioning the medium are taken from a cell line that can proliferate in culture for an extended period, typically at least about 60 days. This does not necessarily mean that the particular cells used for conditioning the medium be long-lived; they can be irradiated or otherwise adapted to limit replication. However, the parent cell line from which they are taken will have the proliferative capacity stated. In particular embodiments, the cell line is an immortalized mouse cell line, or a human cell line, and may have characteristics of a fibroblast or muscle cell line. Exemplary lines are obtained by differentiating human embryonic stem cells ex vivo, and are euploid. Any of these cell lines can be genetically altered to express a growth factor (such as bFGF) or telomerase reverse transcriptase (TERT) at an elevated level.

Another embodiment of this invention is conditioned medium to support culturing pPS cells in a growth environment essentially free of feeder cells, prepared according to a method of this invention. A further embodiment is a composition of proliferating pPS cells or other cells in a growth environment that includes the conditioned medium of this invention, optionally free of feeder cells.

Yet another embodiment of this invention is a human cell line obtained by differentiating a culture of human embryonic stem (hES) cells into a population of differentiated cells that comprises fibroblast-like or mesenchymal cells, and then selecting such cells from the culture. Medium conditioned by culturing with the selected cells supports growth of pPS cells in feeder-free culture. If desired, the cell line can be genetically altered to express TERT at an elevated level.

A further embodiment of the invention is a method for screening cells suitable for producing conditioned medium that supports growth of pPS cells, based on a feeder-free growth environment in which growth of pPS cells without differentiation can be promoted by medium conditioned by primary mouse embryonic fibroblasts (mEF). In the screening method, a test medium conditioned by cells being screened according to the method is used instead, the ability of the test medium to support growth of the pPS is assessed, and the suitability of the medium is correlated with growth of the pPS without substantial differentiation.

Still another embodiment of the invention is a device for preparing conditioned medium, comprising a culture chamber containing cells from a cell line of this invention that can condition medium to render it able to support growth of pPS cells in feeder-free culture; and a port for withdrawing conditioned medium from the culture chamber.

These and other embodiments of the invention will be apparent from the description that follows.

DRAWINGS

FIG. 1 is a copy of photomicrographs showing the morphology of hES cells in feeder-free culture. Panel A (Left Side) shows morphology of hES cells cultured on feeder cells in regular culture medium (mEF/RM), or on Matrigel®, laminin, fibronectin, or collagen IV in mEF conditioned medium. Panel B (Right Side) shows morphology of hES cells maintained on Matrigel® in medium conditioned by mEF, NHG190, STO and BJ cells, compared with unconditioned regular medium (RM). The cells in RPE conditioned medium differentiated within the first week of culture. The cells in the other conditioned media all had hES colonies with appropriate ES-morphology. Panel C is a bar graph showing integrin expression measured in hES cells maintained on feeders in regular medium (mEF/RM) or on Matrigel®; or on laminin in mEF conditioned medium. Integrin components α6 and β1 may play a role in adherence of hES cells to extracellular matrix.

Figure 2:
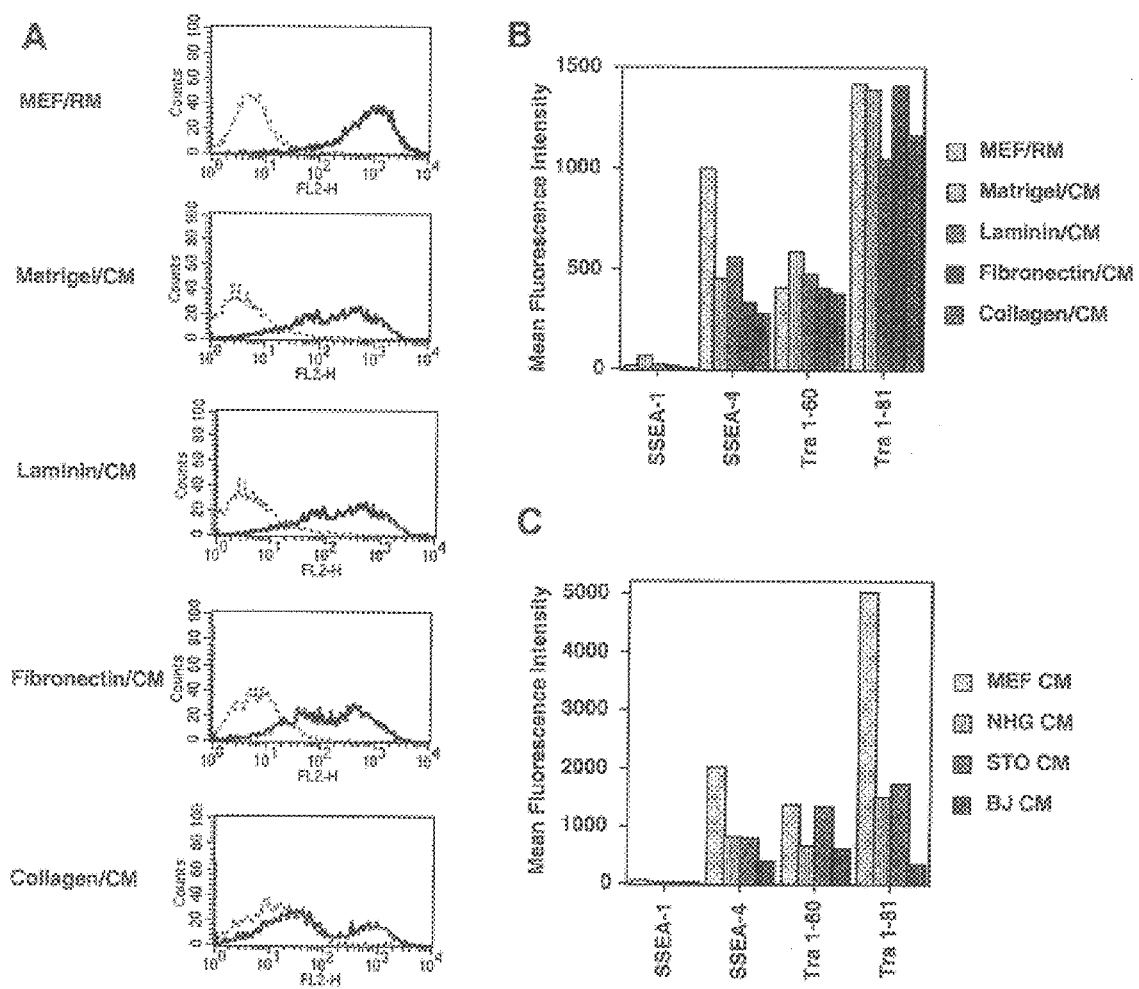

FIG. 2 shows surface marker expression in feeder-free cells by FACS analysis. Panel A is a FACS scan profile showing expression of SSEA-4 (sometimes present on undifferentiated cells) for hES grown on feeders in regular medium (mEF/RM), or on extracellular matrix with conditioned medium. Panel B is a bar graph showing fluorescence intensity of surface markers for hES cells cultured on different matrices. Panel C is a bar graph showing surface markers for hES cells cultured on Matrigel® in conditioned medium from different cell lines.

Figure 3:
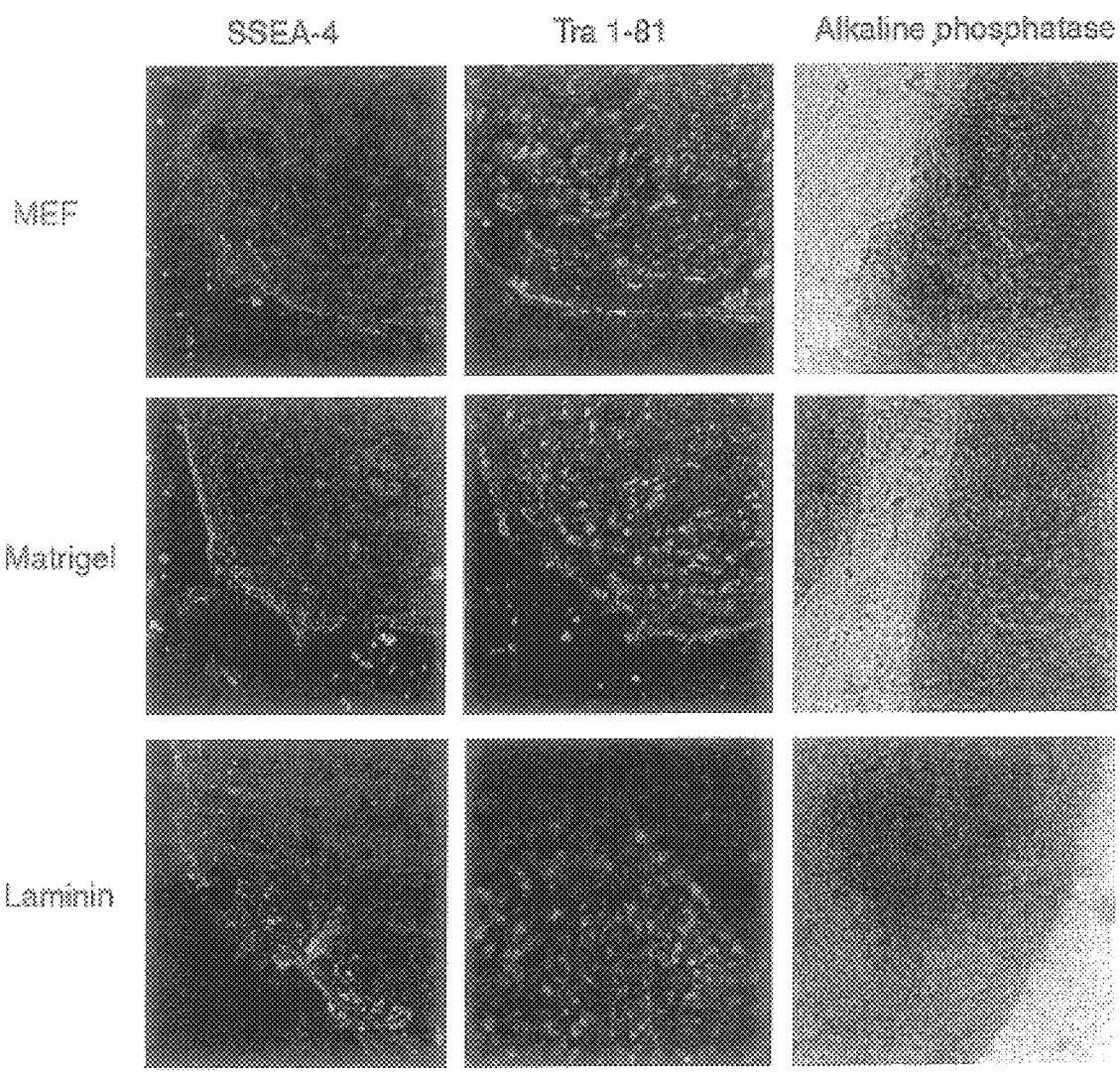

FIG. 3 is a photocopy reproduction of micrographs showing marker expression detected by immunohistochemistry for cells grown with primary feeder cells (mEF) or on the extracellular matrices Matrigel® or laminin. hES cells grown in feeder-free culture have phenotypic markers similar to those of hES grown on mouse fibroblast feeder cells.

Figure 4:
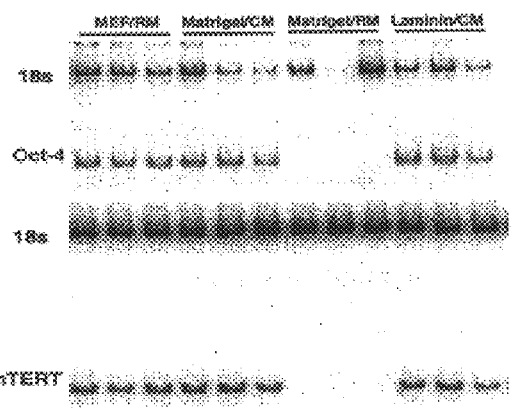
Figure 4:
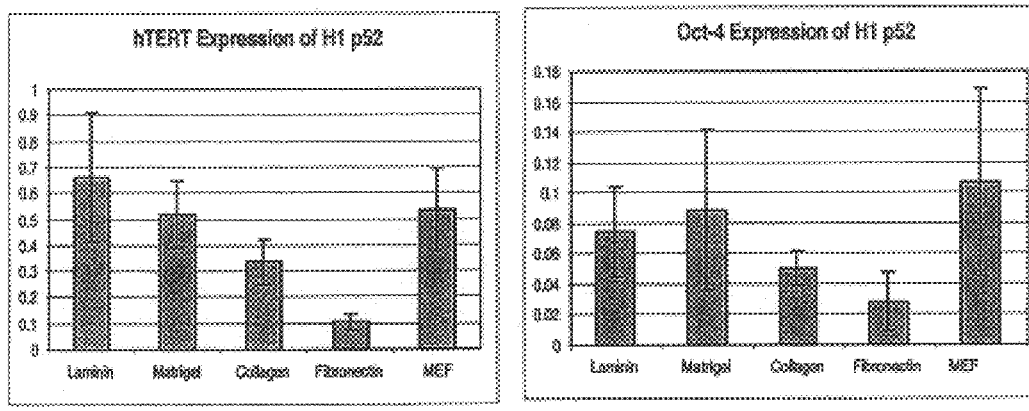

FIG. 4 provides an analysis of Oct-4 and hTERT expression in hES cells cultured with feeder cells (mEF) or extracellular matrix (Matrigel® or laminin) with regular medium (RM) or conditioned medium (CM). The upper panel is a copy of a gel showing Oct-4 and hTERT expression at the mRNA level by RT-PCR. The lower panel is a bar graph comparing the level of expression for cells grown on different substrates, expressed as the ratio of Oct4 or hTERT to the 18s standard. hES cells grown on Laminin and Matrigel® in conditioned medium have similar expression patterns to those of cells grown on a feeder layer.

Figure 5:
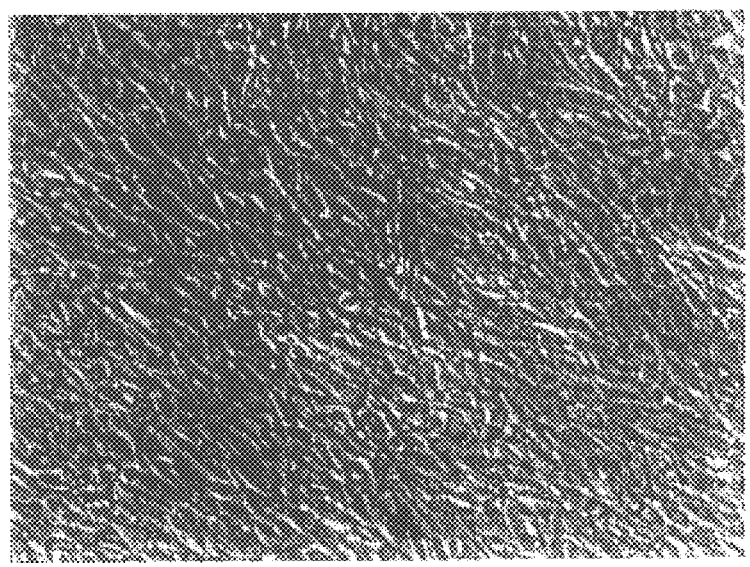
Figure 5:
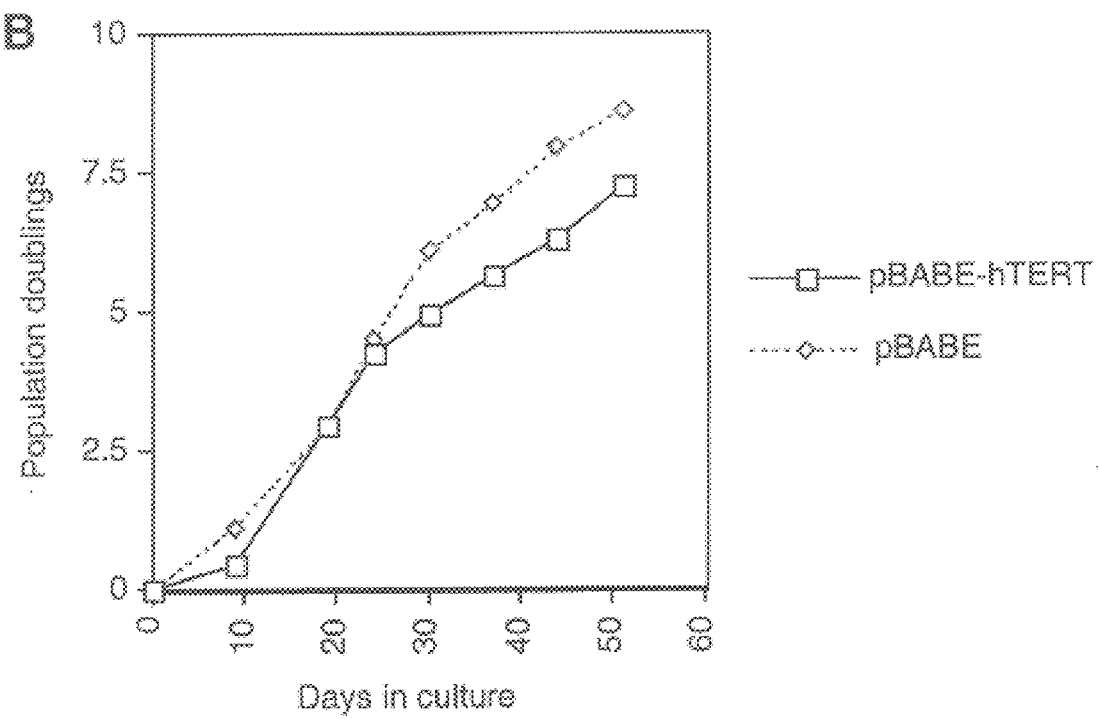

FIG. 5, Panel A, is a copy of a photomicrograph showing the morphology of a human fibroblast-like (hEF) cell line, derived from human embryonic stem cells. These cells have been immortalized by infecting with retrovirus pBABE containing an hTERT expression cassette. Panel B (below) is a line graph showing the growth of the hEF-like cells transduced for expression of the telomerase catalytic subunit, compared with cells transduced with vector control.

Figure 6:
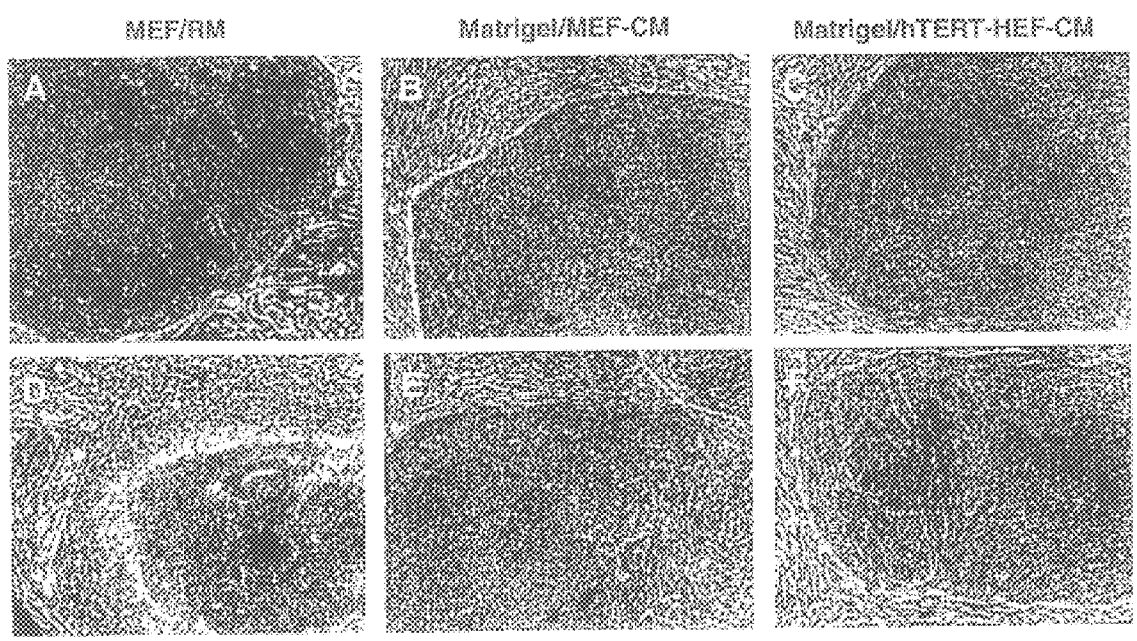

FIG. 6 is a copy of six photomicrographs, comparing human embryonic stem cells maintained in different culture environments. Panels A & D: hES cells grown directly on primary mouse embryonic fibroblasts (mEF). Panels B & E: hES cells in feeder-free culture supported by conditioned medium from primary mEF. Panels C & F: hES cells in feeder-free culture supported by medium from human embryonic fibroblast-like cells (FIG. 5). In each of these conditions, healthy colonies of hES cells increased in size, and had characteristic features of undifferentiated embryonic stem cells.

Figure 7:
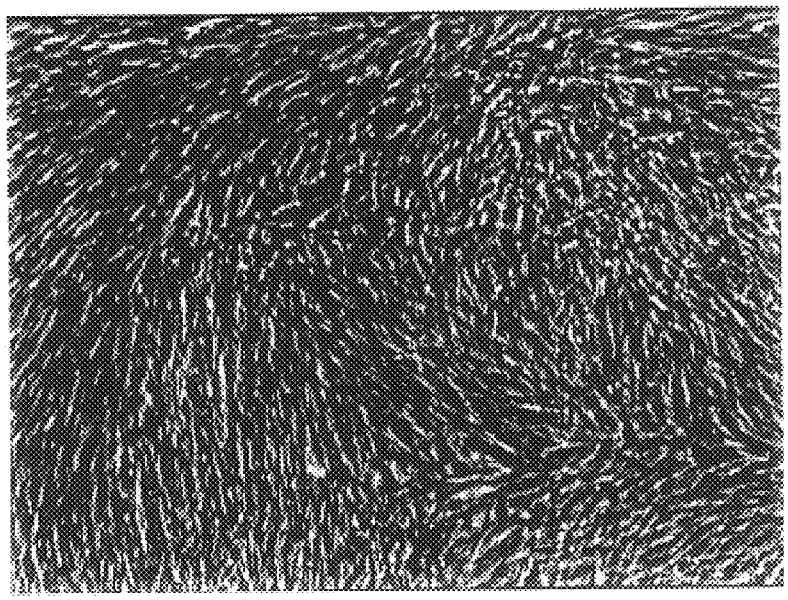
Figure 7:
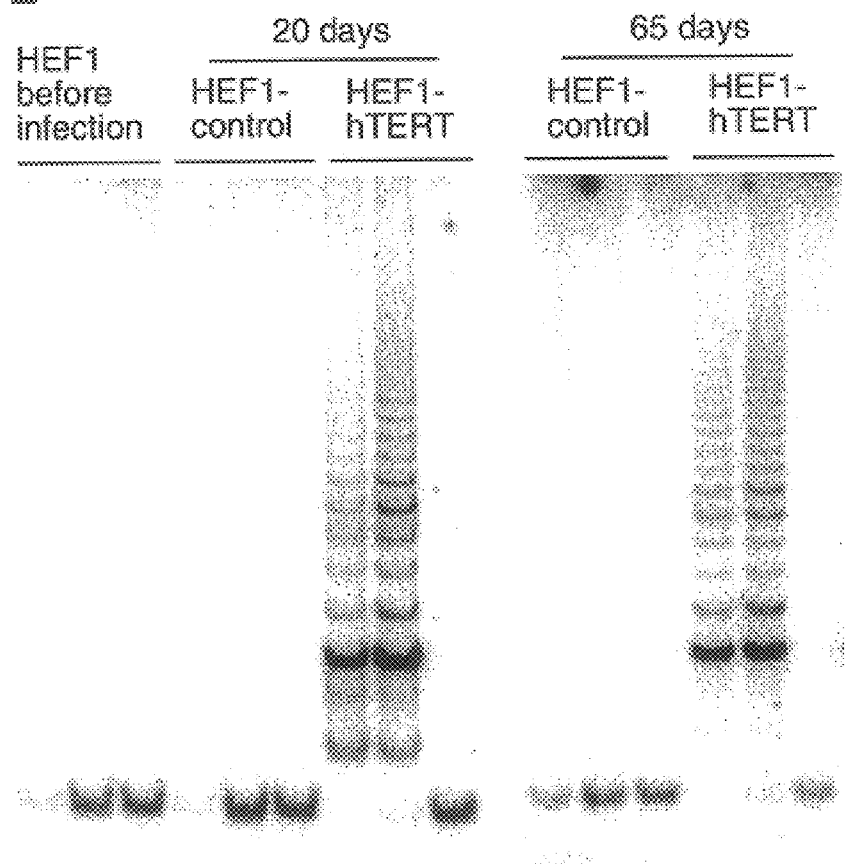

FIG. 7 shows features of a second human cell line capable of producing conditioned medium that supports hES cells in feeder-free culture. Panel A is a copy of a phase contrast micrograph, showing that the HEF1 cell line has morphological characteristics of fibroblasts or mesenchymal cells. Panel B (below) is a copy of the results of a TRAP assay, showing that HEF1 cells transduced with a retroviral vector for telomerase reverse transcriptase (hTERT) acquired telomerase activity.

Figure 8:
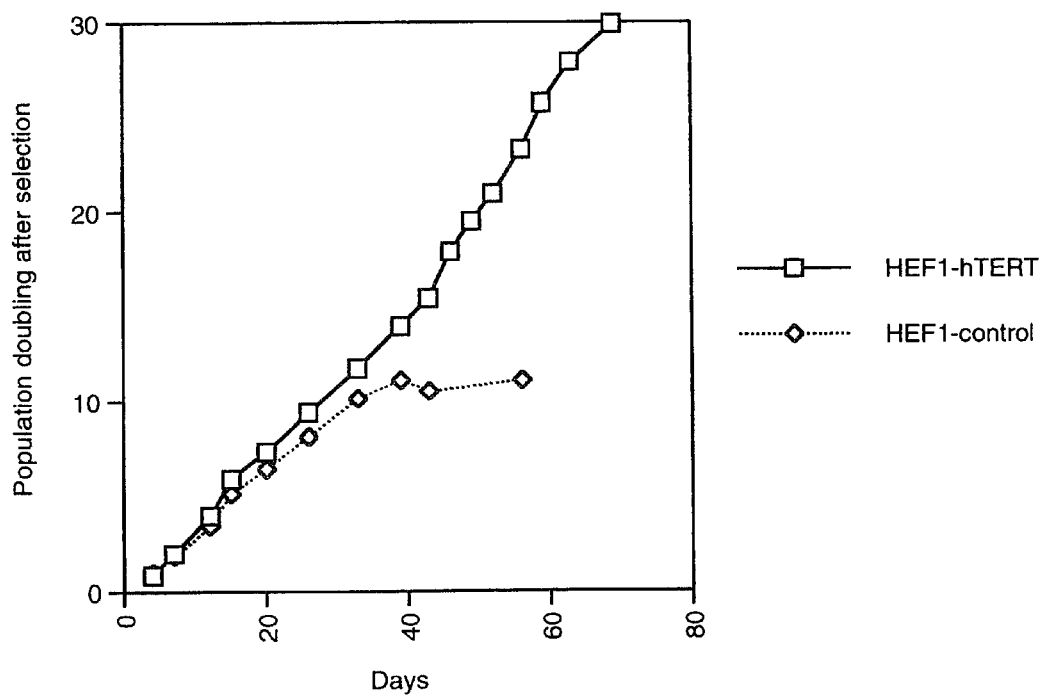

FIG. 8 is a graph showing growth of hTERT-transduced HEF1 cells, and cells transduced with vector control. Both lines initially doubled about once every 2 days. However, the control cells stopped proliferating at 38 days, while the hTERT-transfected cells continued proliferating over 60 days at a consistent growth rate.

Figure 9:
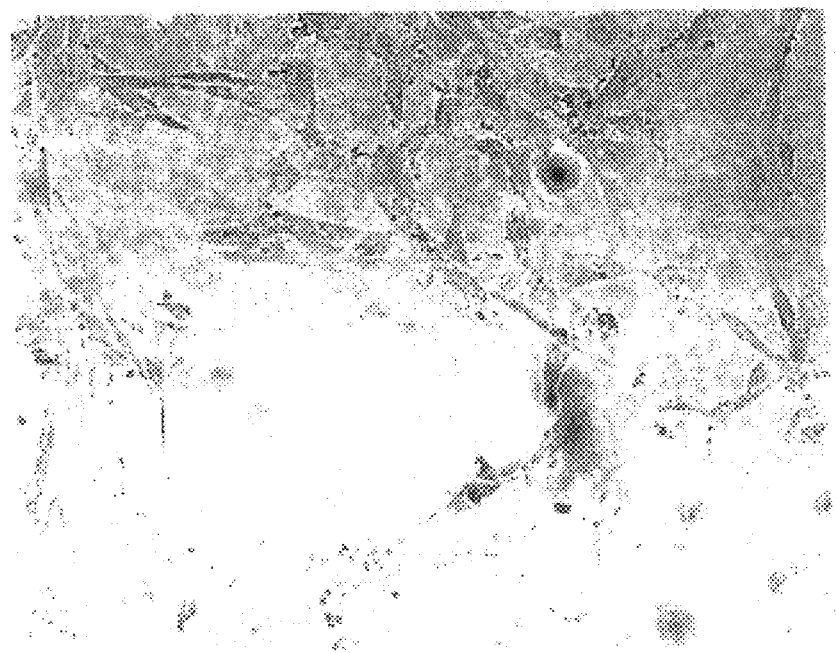
Figure 9:
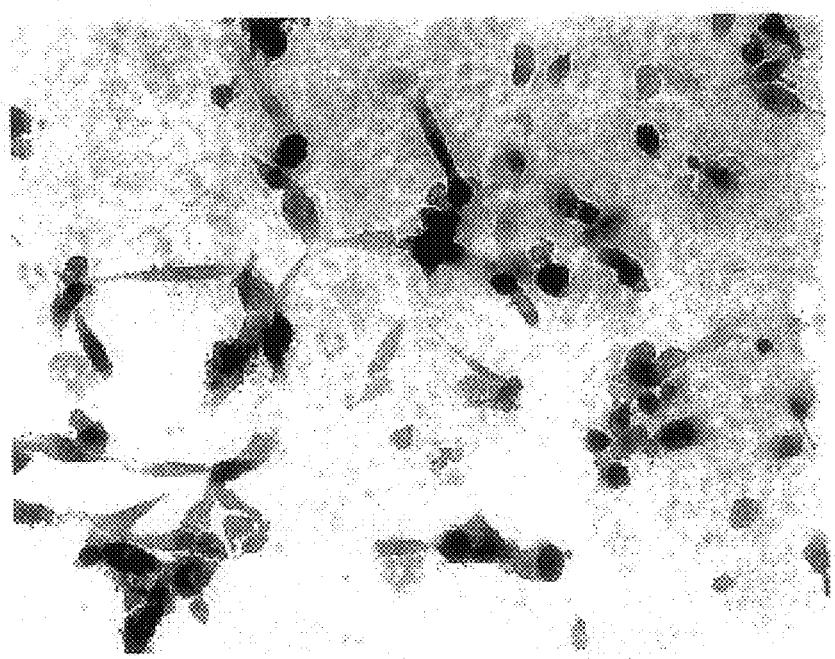

FIG. 9 is a micrograph of the hTERT transduced cells and control cells, after staining for senescence-associated β-galactosidase, a known biomarker for cellular aging. Transfection with hTERT extends the life-span of the cell line and forestalls senescence.

Figure 10:
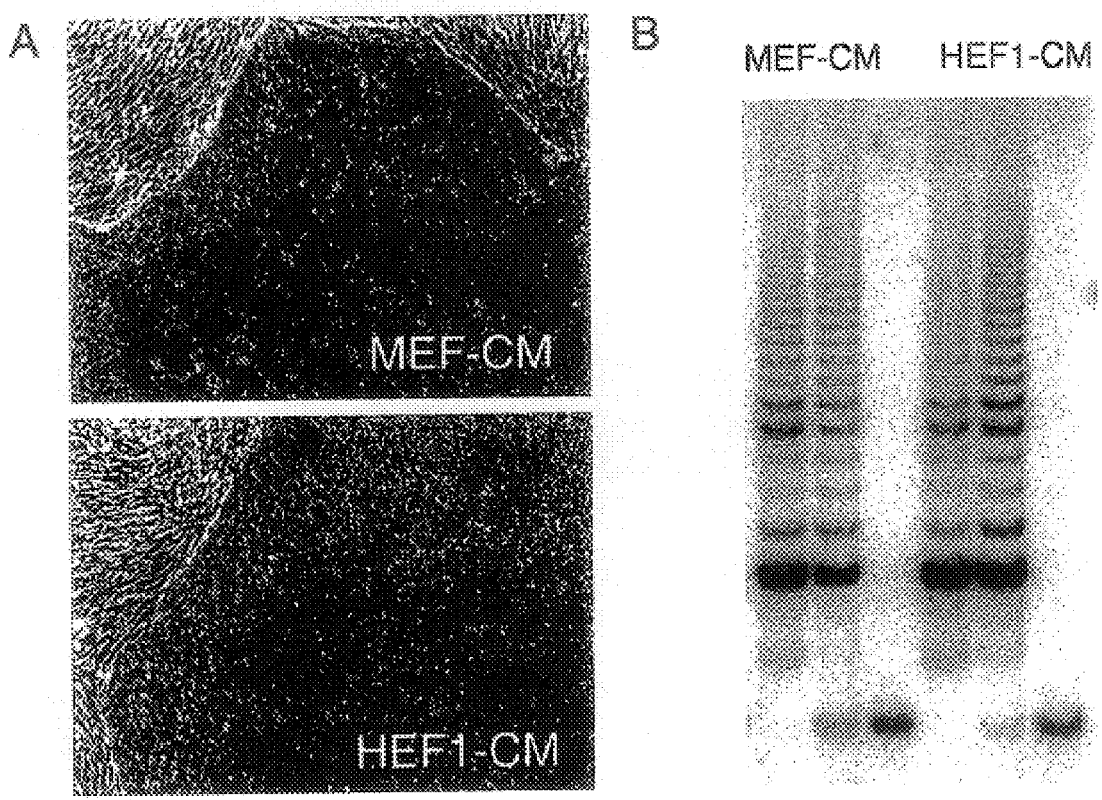

FIG. 10 shows colonies of hES cells after passaging into conditioned medium. Panel A is a copy of a light micrograph, showing undifferentiated colonies in cultures of hES cells maintained in medium conditioned by primary mouse embryonic fibroblasts (mEF), or by the human fibroblast-like cell line HEF1. Panel B (right) is a copy of the results of a TRAP, showing that hES cells maintained using HEF1 conditioned medium show telomerase activity characteristic of undifferentiated cells.

DETAILED DESCRIPTION

This invention provides a system for preparing media that support the growth of primate pluripotent stem (pPS) cells in the absence of feeder cells. Cell lines have been developed that can provide a reliable, effective supply of conditioned media for bulk stem cell culture.

Conventionally, human embryonic stem cells are grown on feeder layers of primary embryonic fibroblasts isolated from mouse (mEFs). As an alternative, they can be grown in feeder-free culture on an appropriate extracellular matrix, using medium conditioned by primary mEFs (Example 2) to supply soluble components provided by the mEFs in feeder culture. Fibroblasts derived from adults are generally not used as feeder cells, suggesting that more mature cells lose the ability to provide the factors requisite to support stem cell growth.

It has now been discovered that feeder cells can be immortalized and maintained in long-term culture without causing them to lose the ability to produce high quality conditioned medium. For example, primary mouse embryonic fibroblasts can be immortalized by genetically altering them to express telomerase reverse transcriptase (Examples 4 and 5). The telomerized mEF line designated NH190 supports the growth of hES cells in feeder-free culture without differentiation through a number of passages (FIG. 1B), and can itself be perpetuated in culture, providing a ready source of high-quality medium.

It has also been discovered that human cells suitable for conditioning medium can be obtained by differentiating embryonic stem cells in vitro. hES cells were differentiated by culturing in suspension for 2 days, and then plating on gelatin-coated plates. Fibroblast-like cells (hEF) were separated from the mixed population and expanded (Example 7). The cell line was found to lack substantial telomerase activity, and some of the cells were transduced with a retrovirus expressing telomerase reverse transcriptase (hTERT). Both the untransduced and the telomerized cell lines proliferated in continual cell culture for over 7 population doublings in 50 days of culture (FIG. 5B).

Cultures of hES cells grown on Matrigel® in hEF conditioned medium formed colonies with morphology characteristic of undifferentiated hES cells (FIG. 7, Panels C & F). The cultures appeared indistinguishable from hES cells grown directly on a layer of primary mEF feeders (Panels A & D). hES cells have proliferated under these conditions for over 30 days without differentiation.

This invention provides a significant advance in technology for producing pluripotent stem cells suitable for commercial distribution:

Availability of established cell lines supporting pPS culture obviates the need to repeatedly prepare primary feeder cultures to continue the culture.

The cell lines of this invention facilitate producing pPS cells on a commercial scale. In comparison with primary feeder cells, they are easier and more economical to maintain and expand.

Media produced by established cell lines are of consistently high quality, and avoid the variability inherent in media obtained from primary cell cultures.

In the context of human therapy, the use of telomerized human cell lines to produce conditioned media is relatively attractive from the perspective of regulatory scrutiny, since these cells contain no xenogeneic components and no components of tumor cell origin.

Those skilled in the art will readily appreciate that pluripotent stem cells cultured using the cell lines and media of this invention provide an important reserve for developing and implementing new therapeutic strategies. A further description follows.

Definitions

Prototype "primate Pluripotent Stem Cells" (pPS cells) are pluripotent cells derived from pre-embryonic, embryonic, or fetal tissue of the stated primate species at any time after gestation, which have the characteristic of being capable under the right conditions of producing progeny of several different cell types. Preferred pPS cells are those capable of producing progeny that are derivatives of all of the three germinal layers: endoderm, mesoderm, and ectoderm, and capable of undergoing proliferation in the absence of feeder cells, as described in this disclosure. Non-limiting exemplars of pPS cells are rhesus and marmoset embryonic stem cells, as described by Thompson et al., Proc. Natl. Acad. Sci. U.S.A. 92:7844, 1995, human embryonic stem (hES) cells, as described by Thomson et al., Science 282:1145, 1998; and human embryonic germ (hEG) cells, described in Shamblott et al., Proc. Natl. Acad. Sci. U.S.A. 95:13726, 1998. Other types of non-malignant pluripotent cells are included in the term. Specifically, any cells that are fully pluripotent (that is, they are those capable of producing progeny that are derivatives of all of the three germinal layers) are included, regardless of whether they were derived from embryonic tissue, fetal tissue, or adult tissue.

pPS cell cultures are said to be "substantially undifferentiated" when they display morphology that clearly distinguishes them from differentiated cells of embryo or adult origin. pPS cells typically have high nuclear/cytoplasmic ratios, prominent nucleoli, and compact colony formation with poorly discernable cell junctions, and are easily recognized by those skilled in the art. It is recognized that colonies of undifferentiated cells can be surrounded by neighboring cells that are differentiated. Nevertheless, the substantially undifferentiated colony will persist when cultured under appropriate conditions, and undifferentiated cells constitute a prominent proportion of cells growing upon splitting of the cultured cells. Useful cell populations described in this disclosure contain any proportion of substantially undifferentiated pPS having these criteria. Substantially undifferentiated cell cultures may contain at least about 20%, 40%, 60%, or even 80% undifferentiated pPS in order of increasing preference (in percentage of total cells in the population).

Whenever a culture or cell population is referred to in this disclosure as proliferating "without differentiation", what is meant is that after proliferation, the composition is substantially undifferentiated state according to the preceding definition. Populations that proliferate through at least 4 passages without differentiation will contain substantially the same proportion of undifferentiated cells (or possibly a higher proportion of undifferentiated cells) when evaluated at the same degree of confluence as the originating culture.

"Feeder cells" or "feeders" are terms used to describe cells of one tissue type that are co-cultured with cells of a tissue type, to provide an environment in which the cells of the second tissue type can grow. The feeder cells are optionally from a different species as the cells they are supporting. For example, certain types of pPS cells can be supported by primary cultures of mouse embryonic fibroblasts, immortalized mouse embryonic fibroblasts, or human fibroblast-like cells differentiated from hES cells, as described later in this disclosure. In coculture with pPS cells, feeder cells are typically inactivated by irradiation or treatment with an anti-mitotic agent such as mitomycin c, to prevent them from outgrowing the cells they are supporting. For use in producing conditioned medium, inactivation of the cells is optional, and depends in part on mechanical aspects of medium production.

pPS cell populations are said to be "essentially free" of feeder cells if the cells have been grown through at least one round after splitting in which substantial fresh feeder cells are not added to support the growth of the pPS. It is recognized that if a previous culture containing feeder cells is used as a source of pPS for the culture to which fresh feeders are not added, there will be some feeder cells that survive the passage. For example, hES cells are often cultured in a 9.6 cm$^2$ well on a surface of ~375,000 primary irradiated embryonic fibroblasts near confluence. By the end of the culture, perhaps 150,000 feeder cells are still viable, and will be split and passaged along with hES that have proliferated to a number of ~1 to 1.5 million. After a 1:6 split, the hES cells generally resume proliferation, but the fibroblasts will not grow and only a small proportion will be viable by the end of ~6 days of culture. This culture is "essentially free" of feeder cells, with compositions containing less than about 5%, 1%, 0.2%, 0.05%, or 0.01% feeder cells (expressed as % of total cells in the culture) being increasingly more preferred.

Whenever a culture or cell population is referred to in this disclosure as "feeder-free", what is meant is that the composition is essentially free of feeder cells according to the preceding definition, subject to further constraints only if explicitly indicated.

A "growth environment" is an environment in which cells of interest will proliferate in vitro. Features of the environment include the medium in which the cells are cultured, the temperature, the partial pressure of $O_2$ and $CO_2$, and a supporting structure (such as a substrate on a solid surface) if present.

A "nutrient medium" is a medium for culturing cells containing nutrients that promote proliferation. The nutrient medium may contain any of the following in an appropriate combination: isotonic saline, buffer, amino acids, antibiotics, serum or serum replacement, and exogenously added factors.

A "conditioned medium" is prepared by culturing a first population of cells in a medium, and then harvesting the medium. The conditioned medium (along with anything secreted into the medium by the cells) may then be used to support the growth of a second population of cells.

The term "antibody" as used in this disclosure refers to both polyclonal and monoclonal antibody. The ambit of the term deliberately encompasses not only intact immunoglobulin molecules, but also such fragments and derivatives of immunoglobulin molecules (such as single chain Fv constructs), and fragments and derivatives of immunoglobulin equivalents such as T-cell receptors, as may be prepared by techniques known in the art, and retaining the desired antigen binding specificity.

For the purposes of this disclosure, a "mesenchymal cell" can be either a terminally differentiated cell or a proliferative precursor cell committed to form cells of a mesenchymal tissue, such as bone, dental tissue, cartilage, tendon, bone marrow stroma, or muscle. Mesenchymal stem cells are included in the term, as are terminally differentiated (postmitotic) cells and more committed replication-competent cells, such as osteoblast precursor cells.

A cell is said to be "genetically altered" or "transformed" when a polynucleotide has been transferred into the cell by any suitable means of artificial manipulation, or where the cell is a progeny of the originally altered cell that has inherited the polynucleotide. The polynucleotide may contain a sequence that is exogenous to the cell, it may contain native sequences in an artificial arrangement (e.g., an encoding region linked to a different promoter), or it may provide additional copies of a native encoding sequence. Unless explicitly stated otherwise, the process of transferring the polynucleotide into the cell can be achieved by any technique suitable for the application at hand, which may include but is not limited to electroporation or liposome-mediated transfer, homologous recombination, transduction or transfection using a viral or bacterial vector. The polynucleotide will often comprise a transcribable sequence encoding a protein of interest, which enables the cell to express the protein at an elevated level. Also included are genetic alterations by any means that result in functionally altering or abolishing the action of an endogenous gene. Suitable methods for effecting such alterations include homologous recombination using a suitable targeting vector (U.S. Pat. Nos. 5,464,764, 5,631,153, 5,789,215, 5,589,369 and 5,776,774).

The genetic alteration is said to be "inheritable" if progeny of the altered cell has the same alteration. Determination of whether the genetic alteration is inheritable can be made by detecting presence of the polynucleotide template (e.g., by PCR amplification), or by detecting a phenotypic feature (such as expression of a gene product or effect thereof) that depends on the genetic alteration to be manifest.

A "cell line" is a population of cells that can be propagated in culture through at least 10 passages. The population can be phenotypically homogeneous, or the population can be a mixture of measurably different phenotypes. Characteristics of the cell line are those characteristics of the population as a whole that are essentially unaltered after 10 passages.

A cell line is from a "non-malignant source" if it was established from primary tissue that is not cancerous, nor from a cell that was genetically altered with a known oncogene. Immortalization of such cells by telomerization maintains their non-malignant status.

A cell is described as "telomerized" if it has been genetically altered with a nucleic acid encoding a telomerase reverse transcriptase (TERT) of any species in such a manner that the TERT is transcribed and translated in the cell. The term also applies to progeny of the originally altered cell that have inherited the ability to express the TERT encoding region at an elevated level. The TERT encoding sequence is typically taken or adapted from a mammalian TERT gene, exemplified by human and mouse TERT, as indicated below.

A cell line is described as "permanent" or "immortalized" if it has at least one of the following properties: 1) it has been genetically altered for elevated expression of telomerase reverse transcriptase (TERT), detectable, for example, as increased telomerase activity in TRAP assay; 2) for cell lines otherwise capable of no more than 15 population doublings, it has been genetically altered to extend its replicative capacity under suitable culture conditions to at least 20 population doublings; or 3) for cell lines otherwise capable of more than 15 population doublings, it has been genetically altered to substantially extend the replicative capacity of the cell line under typical culture conditions. It is understood that cells meeting this definition include not only the original genetically altered cells, but also all progeny of such cells that meet the listed criteria.

General Techniques

For further elaboration of general techniques useful in the practice of this invention, the practitioner can refer to standard textbooks and reviews in cell biology, tissue culture, and embryology. Included are "*Teratocarcinomas and embryonic stem cells: A practical approach*" (E. J. Robertson, ed., IRL Press Ltd. 1987); "*Guide to Techniques in Mouse Development*" (P. M. Wasserman et al. eds., Academic Press 1993); "*Embryonic Stem Cell Differentiation in Vitro*" (M. V. Wiles, Meth. Enzymol. 225:900, 1993); "*Properties and uses of Embryonic Stem Cells: Prospects for Application to Human Biology and Gene Therapy*" (P. D. Rathjen et al., al., 1993). Differentiation of stem cells is reviewed in Robertson, Meth. Cell Biol. 75:173, 1997; and Pedersen, Reprod. Fertil. Dev. 10:31,1998.

Methods in molecular genetics and genetic engineering are described in "*Molecular Cloning: A Laboratory Manual*" 2nd Ed. (Sambrook et al., 1989); "*Oligonucleotide Synthesis*" (M. J. Gait, ed., 1984); "*Animal Cell Culture*" (R. I. Freshney, ed., 1987); the series "*Methods in Enzymology*" (Academic Press, Inc.); "*Gene Transfer Vectors for Mammalian Cells*" (J. M. Miller & M. P. Calos, eds., 1987); "*Current Protocols in Molecular Biology*" and "*Short Protocols in Molecular Biology, 3rd Edition*" (F. M. Ausubel et al., eds., 1987 & 1995); and "*Recombinant DNA Methodology II*" (R. Wu ed., Academic Press 1995). Reagents, cloning vectors, and kits for genetic manipulation referred to in this disclosure are available from commercial vendors such as BioRad, Stratagene, Invitrogen, and ClonTech.

General techniques used in raising, purifying and modifying antibodies, and the design and execution of immunoassays including immunohistochemistry, the reader is referred to *Handbook of Experimental Immunology* (D. M. Weir & C. C. Blackwell, eds.); *Current Protocols in Immunology* (J. E. Coligan et al., eds., 1991); and R. Masseyeff, W. H. Albert, and N. A. Staines, eds., *Methods of Immunological Analysis* (Weinheim: VCH Verlags GmbH, 1993).

General techniques in cell culture and media collection are outlined in *Large Scale Mammalian Cell Culture* (Hu et al., Curr. Opin. Biotechnol. 8:148, 1997); *Serum-free Media* (K. Kitano, Biotechnology 17:73, 1991); *Large Scale Mammalian Cell Culture* (Curr. Opin. Biotechnol. 2:375, 1991); and *Suspension Culture of Mammalian Cells* (Birch et al., Bioprocess Technol. 19:251, 1990). Other reading of interest includes *Understanding Media* (M. McLuhan, Mentor N.Y., 1964) and *The Medium is the Massage* (M. McLuhan & Q. Fiore, Bantam N.Y., 1967).

Preparation of pluripotent stem cells from primate embryonic tissue

Conditioned media described in this application are useful for culturing pluripotent stem cells in the presence or absence of feeder cells. It is recognized that other types of cells may benefit from being cultured in these media, and the compositions of this invention may be used for such purposes without restriction. However, the media (and the cells used to prepare media) have the characteristic of being able to support the growth of primate pluripotent stem cells in culture environments essentially free of feeder cells.

Types of pluripotent stem (pPS) cells that may be used include established lines of pluripotent cells derived from tissue formed after gestation, including pre-embryonic tissue (such as a blastocyst), embryonic tissue, or fetal tissue taken any time during gestation, typically but not necessarily before ~10–12 weeks gestation. Non-limiting exemplars are established lines of hES or hEG cells, described in more detail below. Also contemplated is use of the compositions of this disclosure during the initial establishment or stabilization of such cells, in which case the source cells would be primary pluripotent cells taken directly from the source tissues. Also suitable are cells taken from a pPS cell population already cultured in the absence of feeder cells.

Human embryonic stem (hES) cells can be prepared as described by Thomson et al. (U.S. Pat. No. 5,843,780; Science 282:1145, 1998; Curr. Top. Dev. Biol. 38:133 ff., 1998; Proc. Natl. Acad. Sci. U.S.A. 92:7844, 1995).

Briefly, human blastocysts are obtained from human in vivo preimplantation embryos. Alternatively, in vitro fertilized (IVF) embryos can be used, or one cell human embryos can be expanded to the blastocyst stage (Bongso et al., Hum Reprod 4: 706, 1989). Briefly, human embryos are cultured to the blastocyst stage in G1.2 and G2.2 medium (Gardner et al., Fertil. Steril. 69:84, 1998). Blastocysts that develop are selected for ES cell isolation. The zona pellucida is removed from blastocysts by brief exposure to pronase (Sigma). The inner cell masses are isolated by immunosurgery, in which blastocysts are exposed to a 1:50 dilution of rabbit anti-human spleen cell antiserum for 30 minutes, then washed for 5 minutes three times in DMEM, and exposed to a 1:5 dilution of Guinea pig complement (Gibco) for 3 min (see Solter et al., Proc. Natl. Acad. Sci. U.S.A. 72:5099,1975). After two further washes in DMEM, lysed trophectoderm cells are removed from the intact inner cell mass (ICM) by gentle pipetting, and the ICM plated on mEF feeder layers.

After 9 to 15 days, inner cell mass-derived outgrowths are dissociated into clumps either by exposure to calcium and magnesium-free phosphate-buffered saline (PBS) with 1 mM EDTA, by exposure to dispase or trypsin, or by mechanical dissociation with a micropipette; and then replated on mEF in fresh medium. Dissociated cells are replated on mEF feeder layers in fresh ES medium, and observed for colony formation. Colonies demonstrating undifferentiated morphology are individually selected by micropipette, mechanically dissociated into clumps, and replated. ES-like morphology is characterized as compact colonies with a high nucleus to cytoplasm ratio and prominent nucleoli. Resulting ES cells are then routinely split every 1–2 weeks by brief trypsinization, exposure to Dulbecco's PBS (without calcium or magnesium and with 2 mM EDTA), exposure to type IV collagenase (~200 U/mL; Gibco) or by selection of individual colonies by micropipette. Clump sizes of about 50 to 100 cells are optimal.

Human Embryonic Germ (hEG) cells can be prepared from primordial germ cells present in human fetal material taken about 8–11 weeks after the last menstrual period. Suitable preparation methods are described in Shamblott et al., Proc. Natl. Acad. Sci. U.S.A. 95:13726, 1998 and International Patent Publication WO 98/43679.

Briefly, genital ridges are rinsed with isotonic buffer, then placed into 0.1 mL 0.05% trypsin/0.53 mM sodium EDTA solution (BRL) and cut into <1 mm$^3$ chunks. The tissue is then pipetted through a 100 μL tip to further disaggregate the cells. It is incubated at 37° C. for ~5 min, then ~3.5 mL EG growth medium is added. EG growth medium is DMEM, 4500 mg/L D-glucose, 2200 mg/L mM sodium bicarbonate; 15% ES qualified fetal calf serum (BRL); 2 mM glutamine (BRL); 1 mM sodium pyruvate (BRL); 1000–2000 U/mL human recombinant leukemia inhibitory factor (LIF, Genzyme); 1–2 ng/ml human recombinant basic fibroblast growth factor (bFGF, Genzyme); and 10 µM forskolin (in 10% DMSO).

Ninety-six well tissue culture plates are prepared with a sub-confluent layer of feeder cells cultured for 3 days in modified EG growth medium free of LIF, bFGF or forskolin, inactivated with 5000 rad γ-irradiation. Suitable feeders are STO cells (ATCC Accession No. CRL 1503). ~0.2 mL of primary germ cell (PGC) suspension is added to each of the wells. The first passage is conducted after 7–10 days in EG growth medium, transferring each well to one well of a 24-well culture dish previously prepared with irradiated STO mouse fibroblasts. The cells are cultured with daily replacement of medium until cell morphology consistent with EG cells were observed, typically after 7–30 days or 1–4 passages.

Using conditioned media to support feeder-free stem cell cultures pPS cells are typically cultured on a layer of feeder cells that support the pPS cells in various ways. Without intending any limitation to the claimed invention, it is a hypothesis of this invention that feeder cells secrete soluble factors that promote pPS cell survival or proliferation, or inhibit differentiation.

According to conventional methods, primate PS cells are first derived and supported on primary embryonic fibroblasts of mouse origin (Thomson et al., supra). As adapted in this disclosure, mEFs are irradiated at a dose to inhibit proliferation but permit synthesis of important factors that support hES cells (~4000 rads γ-irradiation), and then plated near confluence. For example, 6-well culture plates can be coated by incubation at 37° C. with 1 mL 0.5% gelatin, and plated with ~375,000 irradiated mEFs per well. Feeder cell layers are used 5 h to 1 week after plating, providing fresh hES medium just before seeding the pPS cells.

As an alternative, it has been found that an artificial growth environment can be used that is essentially free of feeder cells, but nonetheless supports proliferation of pPS cells without undergoing substantial differentiation, as defined earlier. The growth of pPS cells in feeder-free culture without differentiation is supported using a medium conditioned by culturing previously with another cell type. Without intending any limitation of the invention, it is hypothesized that the conditioning process provides an opportunity for the cells to release into the medium soluble factor that replace the role of the feeder cells in promoting pPS cell survival or proliferation, or inhibiting differentiation.

By way of illustration, conditioned medium can be prepared by culturing irradiated primary mouse embryonic fibroblasts at a density of $5 \times 10^5$ cells per 9.6 $cm^2$ well in a serum replacement medium containing 4 ng/mL basic fibroblast growth factor (bFGF). The culture supernatant is typically harvested after 1 day at 37° C., and supplemented with additional growth factors that benefit pPS cell culture.

Other features of the growth environment facilitate pPS proliferation without differentiation. In the absence of feeder cells, the pPS are plated onto a suitable culture substrate. Particularly suitable are extracellular matrix components, such as those derived from basement membrane or that may form part of adhesion molecule receptor-ligand couplings. A commercial preparation is available from Becton Dickenson under the name Matrigel®, and can be obtained in a Growth Factor Reduced formulation. Both formulations are effective. Matrigel® is a soluble preparation from Engelbreth-Holm-Swarm tumor cells that gels at room temperature to form a reconstituted basement membrane.

Other extracellular matrix components and component mixtures are suitable as an alternative. Depending on the cell type being proliferated, this may include laminin, fibronectin, proteoglycan, entactin, heparan sulfate, and the like, alone or in various combinations. Laminins are major components of all basal laminae in vertebrates, which interact with integrin heterodimers such as $\alpha 6\beta 1$ and $\alpha 6\beta 4$ (specific for laminins) and other heterodimers (that cross-reach with other matrices).

The pluripotent cells are plated onto the substrate in a suitable distribution and in the presence of a medium that promotes cell survival, propagation, and retention of the desirable characteristics. All these characteristics benefit from careful attention to the seeding distribution. One feature of the distribution is the plating density. It has been found that plating densities of at least about 20,000 cells $cm^{-2}$ promote survival and limit differentiation. Typically, a plating density of between about 90,000 $cm^{-2}$ and about 170,000 $cm^{-2}$ is used.

Another feature is the dispersion of cells. The propagation of mouse stem cells involves dispersing the cells into a single-cell suspension (Robinson, Meth. Mol. Biol. 75:173, 1997 at page 177). In contrast, the passage of pPS cells in the absence of feeders benefits from preparing the pPS cells in small clusters. Enzymatic digestion is halted before cells become completely dispersed, and the cells are triturated with the pipette until they are suspended as clumps of adherent cells, about 10–200 cells in size. The clumps are then plated directly onto the substrate without further dispersal.

Selecting cells suitable for conditioning media

Conditioned medium can be tested for its ability to support pPS cells by culturing pPS cells in a feeder-free growth environment where they grow without differentiation when supported by medium conditioned by primary mouse embryonic fibroblasts (mEF), but using the test medium instead. If pPS cells grow in a substantially undifferentiated state, then the conditioned medium can be characterized as supporting pPS cells in feeder free culture.

A convenient way to determine whether pPS cells are differentiating is to follow the morphological features of the colonies. For example, characteristic morphological features of undifferentiated hES cells are known by those skilled in the art, and include high nuclear/cytoplasmic ratios, prominent nucleoli, and compact colony formation with poorly discernable cell junctions. During passage, some cells may differentiate (particularly when replated as single cells, or when large clusters are allowed to form). However, cultures typically reestablish a larger proportion of undifferentiated cells during the culture period. Ideally, the propagated cells will have a doubling time of no more than about 20–40 hours.

According to this assay method, conditioned medium will be considered capable of supporting growth of pPS cells if the proportion of undifferentiated pPS cells in a subconfluent culture (typically ~5 days after passaging) does not substantially decline through at least 4 passages in the conditioned medium (optionally supplemented with additional growth factors or otherwise processed as appropriate). Determination that the pPS cells are undifferentiated can be done by morphological criteria, and confirmed by demonstrating expression of Oct-4 and/or TERT.

If desired, a quantitative readout of this assay can be obtained to estimate the quality or concentration of pPS cell supportive factors in the medium. In one example, basal medium is conditioned for various periods of time (say, 6 h, 12 h, 24 h, and 48 h), and the conditioned media are each tested for their ability to support feeder-free pPS cell culture for consecutive 24 h periods. Media rendered effective by briefer conditioning periods are increasingly more preferred. In another example, basal medium conditioned for 24 h is tested by dilution analysis (diluting in basal medium, optionally supplemented with other nutrients) for its ability to support pPS culture. Media that are effective after greater dilution (for example, 1:1, 1:2, and 1:4 conditioned medium:diluent medium) are increasingly more preferred. Other variables that can be refined include the plating density of the cells, whether or not they are inactivated (e.g., by irradiation or with mitomycin c), and conditions for filtering the media.

Cell lines can be tested for their ability to produce conditioned medium by culturing the cells in a basal medium for an appropriate time, and then testing the medium for its ability to support feeder-free pPS cell cultures as described above. If the conditioned medium does not support feeder-free pPS cultures, the method of conditioning can be adjusted in various parameters, such as culture time, basal medium used, cell density, and possible post-culture processing of the medium or supplementation with additional additives. Adjustment of these and other parameters can be performed empirically, and as a matter of routine experimentation. A cell line will be considered to have passed the test if it produces conditioned medium that support feeder-free pPS cultures after routine optimization of any of the culture parameters during conditioning.

If desired, conditioned media and cells for producing them can be further evaluated based on other characteristics of the pPS cells they support. For example, pPS cells can be further characterized based on expressed cell markers. Tissue-specific markers can be detected using a suitable immunological technique—such as flow cytometry for membrane-bound markers, immunohistochemistry for extracellular or intracellular markers, and enzyme-linked immunoassay, for markers secreted into the medium. The expression of protein markers can also be detected at the mRNA level by reverse transcriptase-PCR using marker-specific primers. See U.S. Pat. No. 5,843,780 for further details.

Under the microscope, ES cells appear with high nuclear/cytoplasmic ratios, prominent nucleoli, and compact colony formation with poorly discernable cell junctions. Primate ES cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of hES cells in vitro results in the loss of SSEA-4, Tra-1-60, and Tra-1-81 expression (if present) and increased expression of SSEA-1. Undifferentiated hES cells typically have alkaline phosphatase activity, which can be detected by fixing the cells with 4% paraformaldehyde, and then developing with Vector Red as a substrate, as described by the manufacturer (Vector Laboratories, Burlingame Calif.) Undifferentiated hES cells also typically express Oct-4 and TERT, as detected by RT-PCR (Example 3).

Another desirable phenotype of propagated pPS cells is a potential to differentiate into cells of all three germinal layers: endoderm, mesoderm, and ectoderm tissues. Pluripotency of hES cells can be confirmed by injecting cells into SCID mice, fixing the teratomas that form using 4% paraformaldehyde, and then examining them histologically for evidence of cell types from the three germ layers. Propagated pPS lines can be karyotyped using a standard G-banding technique and compared to published karyotypes of the corresponding primate species. It is desirable to obtain cells that have a "normal karyotype", which means that the cells are euploid, wherein all human chromosomes are present and not noticeably altered.

Exemplary non-human cell lines

Feeder cells typically contain fibroblast type cells. Primary embryonic or fetal feeder cell cultures are a mixed population of cells, containing cells that have morphology of fibroblasts and of early muscle cells. Different cells in the population may play different roles in supporting pPS culture, and the distribution and character of the culture may change.

More permanent feeder cell lines can be obtained for producing medium according to this invention by obtaining embryonic fibroblasts from a non-human species such as a mouse. The cells are then genetically altered with an immortalizing gene, such as a gene that expresses telomerase. The altered cell line can then be passaged or frozen for future use in preparing cultured medium. To use the cells in supporting pPS in a feeder culture, the feeder cells are plated to near confluence, irradiated to prevent proliferation, and then layered with small clumps of pPS cells that have either been freshly isolated or passaged from previous culture.

Mouse embryonic fibroblasts (mEF) can be obtained from outbred CF1 mice (SASCO) or other suitable strains. In an illustrative method, the abdomen of a mouse at 13 days of pregnancy is swabbed with 70% ethanol, and the decidua is removed into phosphate buffered saline (PBS). Embryos are harvested; placenta, membranes, and soft tissues are removed; and the carcasses are washed twice in PBS. They are then transferred to fresh 10 cm bacterial dishes containing 2 mL trypsin/EDTA, and finely minced. After incubating 5 min at 37° C., the trypsin is inactivated with 5 mL DMEM containing 10% FBS, and the mixture is transferred to a 15 mL conical tube. Debris is allowed to settle for 2 min, the supernatant is made up to a final volume of 10 mL, and plated onto a 10 cm tissue culture plate or T75 flask. The flask is incubated undisturbed for 24 h, after which the medium is replaced. When flasks are confluent (~2–3 d), they are split 1:2 into new flasks. Mouse embryonic fibroblasts can be propagated in mEF medium, containing 90% DMEM (Gibco # 11965-092), 10% FBS (Hyclone # 30071-03), and 2 mM L-glutamine. T150 flasks are used (Corning # 430825), splitting the cells 1:2 every other day with trypsin, to keep the cells subconfluent.

If desired, the cells used for conditioning medium can be genetically altered to provide one or more additional features. For example, for screening purposes, cells can be provided with drug resistance genes for one or more antibiotics, such as neomycin, hygromycin, or puromycin (Example 5). Cells can be provided with marker genes, such as green fluorescent protein (Example 5), β-galactosidase, or certain cell-surface antigens (such as a truncated NGF receptor) that provide a tag for immunoisolation. Cells can also be provided with genes for the biosynthesis and secretion of factors that supplement the potency of the medium for supporting pPS culture. Exemplary is human basic fibroblast growth factor (bFGF), and other nutritional supplements listed in this disclosure.

To increase the replicative capacity of a cell line used for conditioning medium, it can be telomerized. Cells are telomerized by genetically altering them with a suitable vector, as described elsewhere in this disclosure, so that they express the telomerase catalytic component (TERT) at an elevated level. Particularly suitable is the catalytic component of human telomerase (hTERT), provided in International Patent Publication WO 98/14592. For some applications, other TERT sequences can be used (mouse TERT is provided in WO 99/27113).

Typically, the vector will comprise a TERT encoding region under control of a heterologous promoter that will promote transcription in the cell line. For example, sequences that can drive expression of the TERT coding region include viral LTRs, enhancers, and promoters (such as MPSV, SV40, MoLV, CMV, MSCV, HSV TK), eukaryotic promoters (such as β-actin, ubiquitin, EF1a, PGK) or combinations thereof (for example, the CMV enhancer combined with the β-actin promoter). Expression of a marker gene can be driven by the same promoter as the TERT gene, either as a separate expression cassette, as part of a polycistronic transcript (in which the coding regions of TERT and the marker gene are separated by an IRES sequence, allowing both individual proteins to be made from a single transcript driven by a single promoter), or as part of the same cassette (a fusion between the coding regions of both TERT and the marker gene, producing a protein that provides the functions of both TERT and the marker gene). Transfection and expression of telomerase in human cells is described in Bodnar et al., Science 279:349, 1998 and Jiang et al., Nat. Genet. 21:111, 1999.

Before and after telomerization, telomerase activity and hTERT expression can be determined using standard reagents and methods. For example, pPS cells are evaluated for telomerase using TRAP activity assay (Kim et al., Science 266:2011, 1997; Weinrich et al., Nature Genetics 17:498, 1997). hTERT expression can also be evaluated by RT-PCR.

Other methods of immortalizing cells are also contemplated, such as genetically altering the cells with DNA encoding the SV40 large T antigen (U.S. Pat. No. 5,869,243, International Patent Publication WO 97/32972), infecting with Epstein Bar Virus, introducing oncogenes such as myc and ras, introducing viral replication genes such as adenovirus E1a, and fusing cells having the desired phenotype with an immortalized cell line. Transfection with oncogenes or oncovirus products is usually less suitable when the cells are to be used for therapeutic purposes.

Exemplary human cell lines

It has been discovered that cells with particular characteristics differentiated from human embryo derived cells can be used to support culture of undifferentiated hPS cells. Many types of fibroblast-like cells derived from human embryo cells have this property, and can be identified according to the assay described earlier.

An exemplary method for obtaining suitable cells involves differentiating a culture of pPS cells (such as hES cells). Differentiated cells with a particular phenotype are selected from amongst the mixed differentiated cell population, and medium conditioned by culturing with the selected cells is tested for its ability to support growth of pPS cells in a culture environment essentially free of feeder cells.

Differentiation of the pPS cells can be initiated by first forming aggregates, for example, by overgrowth of a donor pPS cell culture, or by culturing pPS cells in culture vessels having a substrate with low adhesion properties that allows embryoid bodies (EB) to form. Embryoid bodies can be made in suspension culture: undifferentiated pPS cells are harvested by brief collagenase digestion, dissociated into clusters, and plated in non-adherent cell culture plates. The aggregates are fed every few days, and then harvested after a suitable period, typically 4–8 days. The cells are then cultured in a medium and/or on a substrate that promotes enrichment of medium-conditioning cells. Alternatively, the cells can be obtained by direct differentiation of pPS cells by preparing a suspension of undifferentiated pPS cells, and then plating directly onto a substrate that promotes regulated differentiation into medium-conditioning cells. Suitable substrates include glass or plastic coverslips that coated with a polycationic substance, such as poly-ornithine, or an extracellular matrix.

Once differentiated, the population can be enriched for medium-conditioning cells either according to markers they express (for example, by immunolabeling and fluorescence sorting, by sorting on magnetic beads, or by immune-specific lysis of contaminating cells).

It has been discovered that mesenchymal or fibroblast-like cells differentiated from hES cells are especially appropriate for conditioning medium according to this invention. Mesenchymal cells and fibroblasts can be recognized by morphological criteria. Relatively undifferentiated mesenchymal cells have mononuclear ovoid, stellate shape or spindle shape, with a round to oval nucleus and a poorly defined cell border. The oval elongate nuclei typically have prominent nucleoli and a mix of hetero- and euchromatin. Fibroblast-like cells have a stellate or spindle shape, with cytoplasmic processes that resemble those of fibroblasts found in connective tissue. Further confirmation of the mesenchymal or fibroblast nature of a cell can be obtained by markers and secreted products of the cell, such as collagen matrix, collagenase, and various isotypes of fibroblast growth factor, particularly bFGF.

Differentiated pPS cells can then be tested according to the assay outlined above, to determine if they are suitable for conditioning medium in such a manner that the medium supports pPS cell growth in feeder-free culture.

Cell lines differentiated and selected from hES in this manner typically are capable of replicating in cell culture for at least about 30 days (Example 7; FIG. 5(B)). In some embodiments, the cells may replicate for at least ~60 days or 120 days (~10 doublings, 25 doublings, or 50 doublings). If desired, the cells can also be genetically altered to express telomerase reverse transcriptase at an elevated level, or otherwise immortalized as described earlier.

Optionally, differentiated human ES cells suitable for conditioning medium can be further adapted—for example, by genetically altering to express a growth factor like bFGF, or to express TERT, or to immortalize the cells, as described in the previous section.

The reader will appreciate that cell lines derived from pPS cells have a variety of potential commercial applications, of which conditioning medium is only the first example. Fibroblast-like cells and mesenchymal cells are useful for in vitro testing of pharmaceutical compositions and genetic constructs, they can be used to support culture of other cells, and they can be incorporated into cellular compositions designed for tissue regeneration in vivo.

Producing conditioned media

A conditioned medium of this invention is produced by culturing cells in the medium, and then harvesting the conditioned medium from the cell culture.

The cells used for the conditioning have the ability to condition medium in a manner that gives it the capacity to support pPS cells in feeder-free form, as described earlier. The base medium used for conditioning can have any of several different formulae, depending in part on the types of cells used. The medium must be able to support culture of at least the cell line used for the conditioning of the medium.

It is convenient that the medium also support culture of pPS after conditioning. However, as an alternative, the medium can be supplemented with other factors or otherwise processed after conditioning to adapt it for culturing the pPS cells.

For supporting pPS cells in feeder-free culture, suitable base media can be made from the following components: Dulbecco's modified Eagle's medium (DMEM), Gibco # 11965-092; Knockout Dulbecco's modified Eagle's medium (KO DMEM), Gibco # 10829-018; Ham's F12/50% DMEM basal medium; 200 mM L-glutamine, Gibco # 15039-027; non-essential amino acid solution, Gibco 11140-050; β-mercaptoethanol, Sigma # M7522; human recombinant basic fibroblast growth factor (bFGF), Gibco # 13256-029. Exemplary serum-containing ES medium is made with 80% DMEM (typically KO DMEM), 20% defined fetal bovine serum (FBS) not heat inactivated, 1% non-essential amino acids, 1 mM L-glutamine, and 0.1 mM p-mercaptoethanol. The medium is filtered and stored at 4° C. for no longer than 2 weeks. Serum-free ES medium is made with 80% KO DMEM, 20% serum replacement, 1% non-essential amino acids, 1 mM L-glutamine, and 0.1 mM β-mercaptoethanol. Not all serum replacements work; an effective serum replacement is Gibco # 10828-028 (proprietary formula; product obtainable from the manufacturer). The medium is filtered and stored at 4° C. for no longer than 2 weeks. Just before combining with the cells used for conditioning, human bFGF can be added to a final concentration of 4 ng/mL.

The selected medium is then combined with the cells used for conditioning in an environment that allows the cells to release into the medium the components that support pPS cells. Optionally, the cells can be inactivated (i.e., rendered incapable of substantial replication) by radiation (e.g., ~4,000 rads), treatment with a chemical inactivator like mitomycin c, or by any other effective method. The inactivation of the cells is not necessary in instances where the medium is separated from the conditioning cells before use in supporting hPS cell cultures.

The cells are cultured in the medium for sufficient time to allow adequate concentration of released factors (or consumption of media components) to produce a medium that supports the culturing of pPS cells without differentiation. Typically, medium conditioned by culturing for 24 h at 37° C. produces medium that supports pPS cell culture for 24 hours. However, the culturing period can be adjusted upwards or downwards, determining empirically (or by assaying for the concentration of essential factors) what constitutes an adequate period. After collecting a batch of conditioned medium, the cells can be used to condition a further batch of medium over a further culture period, for as many cycles as desired as long as the cells retain their ability to condition the medium in an adequate fashion. For example, fibroblast-like cells derived from differentiation of embryonic stem cells can be used to condition medium over 1-day periods for 1–2 weeks (Example 8).

Selection of culture apparatus for conditioning medium can be made based on the scale and purpose of medium collection. In initial studies and for screening purposes, it is often convenient to produce cultured medium in standard culture flasks or multi-well plates. Large scale, automated, or GMP compliant production can involve the use of specialized devices.

Continuous cell culture systems are reviewed by J. Furey (Genetic Eng. News 20:10, May 15, 2000). Perfusion culture involves removal of medium from the culture chamber, and replenishment with fresh medium. In the spin basket system, a basket-like device is attached to a drive shaft and covered by a porous screen through which medium can be exchanged. In the external filter perfusion system, a culture is circulated from a vessel, through a hollow-fiber filter module, and back to the vessel, with a pump attached to the loop to provide the circulation. A particular perfusion system, the ATF System (available commercially from Refine Technology, Edison N.J.) consists of a diaphragm pump on one end of a hollow-fiber housing, the other end of which is connected to a bioreactor. Alternating tangential flow through the fibers generates low shear laminar flow, which provides high flow rates, scalability, and adaptability to different bioreactors.

Large-scale culture systems are also available from Aastrom Sciences Inc., Ann Arbor Mich. The AastromReplicell™ System provides for expansion from small starting cell populations (Koller et al., Bone Marrow Transpl. 21:653, 1009; Koller et al., Blood 86:1784,1995). Cellstasis® culture technology is marketed by Genespan Corp., Bothell Wash. Cells reside in extracapilliary spaces, and hollow fibers bring fresh media and oxygen into the culture environment (R. Lewis, Genetic Eng. News18(9), May 1, 1998). Any other suitable device can be used with this invention. U.S. Pat. No. 4,501,815 describes a device for culturing differentiated cells. U.S. Pat. No. 4,296,205 describes cell culture and continuous dialysis flasks and their use. U.S. Pat. No. 5,994,129 describes a portable cassette for use in maintaining biological cells. U.S. Pat. No. 5,362,642 describes a containment system for storing, reconstituting, dispensing, and harvesting cell culture media. U.S. Pat. No. 6,022,742 describes a culture device and method.

A particular embodiment of this invention is a device adapted for preparing conditioned medium, having a culture chamber containing cells of this invention capable of conditioning medium, and an outlet port that is optionally sealable for withdrawing medium from the culture chamber after conditioning by the cells. The device may also have a mass-transfer microporous surface in the form of a plate, a hollow fiber, or other structure that partitions the cultured cells from medium that has been conditioned, which allows free passage of the medium, and which provides passage to the outlet port. The device may also have one or more ports for introducing fresh medium, introducing additional cells, or removing expired cells and cell debris. For continuous flow systems, a pump may be attached to the medium inlet or outlet port to provide circulation.

In certain embodiments, the conditioned medium is supplemented before use with additional growth factors that benefit pPS cell culture. For hES cells, a growth factor like bFGF or FGF-4 is often used. It has been found that the ability of the medium to support hES cells in feeder-free culture may benefit by adding bFGF both before and after the conditioning of the medium (Example 6). For hEG cells, culture medium may be supplemented with a growth factor like bFGF, an activator of gp130, such as LIF, IL-6, or Oncostatin-M, and perhaps a factor that elevates cyclic AMP levels, such as forskolin or cholera toxin. Other types of pPS cells may benefit from other factors in the medium, such as stem cell factor (also known as Steel factor, c-kit ligand).

In one illustration, medium containing 20% serum replacement plus 4 ng/mL bFGF is conditioned by culturing ~24 h with the irradiated conditioning cells of the HEF1 line (Example 9). The medium is then filtered through a 0.22 μm membrane, and supplemented with further 8 ng/mL bFGF (adjusted to compensate for bFGF adsorbed during filtering).

If desired, the conditioned medium can be processed further. For example, it can be concentrated by salt filtration or selective filtration, or it can be extracted to separate or store the effective components. Medium extracts can then be reconstituted or supplemented with fresh culture medium before use.

After preparation, the medium can be used to support pPS cells in feeder-free culture, as described earlier, or stored frozen for future use. It is also suitable for other purposes, and can be used for such purposes without restriction. For example, the medium can be added to pPS cultured in the presence of feeder cells, in order to further support the proliferation of the cells or limit differentiation. The medium can also be used to maintain or promote proliferation of other types of cultured precursor cells or terminally differentiated cells, as may be determined empirically.

Use of pPS cells propagated with conditioned media

This description provides a system by which a sizeable quantity of pluripotent cells can be produced commercially without the need of feeder cells. These cell populations can be used for a number of important purposes.

For example, pPS cells maintained without feeder cells can be used to prepare antibody that is specific for embryo markers, stem cell markers, germ cell markers, and other antigens that may be expressed on the cells. Polyclonal antibodies can be prepared by injecting a vertebrate animal with cells of this invention in an immunogenic form. Production of monoclonal antibodies is described in such standard references as U.S. Pat. Nos. 4,491,632, 4,472,500 and 4,444,887, and Methods in Enzymology 73B:3 (1981). Specific antibody molecules can also be produced by contacting a library of immunocompetent cells or viral particles with the target antigen, and growing out positively selected clones. See Marks et al., New Eng. J. Med. 335:730, 1996, and McGuiness et al., Nature Biotechnol. 14:1449, 1996. A further alternative is reassembly of random DNA fragments into antibody encoding regions, as described in EP patent application 1,094,108 A.

pPS cells maintained without feeders can also be used to prepare a cDNA library relatively uncontaminated with cDNA from feeder cells. mRNA is prepared by standard techniques (Sambrook et al., supra) from the pPS cells. After reverse transcribing into cDNA, the preparation can be subtracted with nucleotides from embryonic fibroblasts and other cells of undesired specificity, to produce cDNA more specifically expressed in pPS cells.

pPS cells can be used to screen for factors (such as small molecule drugs, peptides, polynucleotides, and the like) or conditions (such as culture conditions or manipulation) that affect the characteristics of cells in feeder-free culture. This system has the advantage of not being complicated by a secondary effect caused by perturbation of the feeder cells by the test compound. In one application, growth affecting substances are tested by withdrawing the, conditioned medium, and then culturing with different cocktails of soluble factors to determine if the treated cells are maintained and proliferate in a satisfactory manner. Potential toxins can be tested in conditioned or regular medium by determining whether cells treated are adversely affected. Potential differentiation factors or conditions can be tested by treating the cells according to the test protocol, and then determining whether the treated cell develops functional or phenotypic characteristics of a differentiated cell of a particular lineage.

pPS cells grown in feeder-free culture can also be differentiated into restricted developmental lineage cells, or terminally differentiated cells. Differentiation of the pPS can be initiated by allowing overgrowth of undifferentiated pPS cell cultures, forming embryoid bodies in suspension culture, or plating pPS cells under conditions that promote differentiation in a particular manner. Such conditions may include withdrawing or adding nutrients, growth factors or cytokines to the medium, changing the oxygen pressure, or altering the substrate on the culture surface (for example, from an extracellular matrix to a polycation such as polyornithine).

Scientists at Geron Corporation have discovered that culturing pPS cells or embryoid body cells in the presence of ligands that bind growth factor receptors promotes enrichment for neural precursor cells. The growth environment may contain a neural cell supportive extracellular matrix, such as fibronectin. Suitable growth factors include EGF, bFGF, PDGF, IGF-1, noggin, and follistatin. Under the appropriate circumstances, populations of cells enriched for expression of the A2B5 marker have the capacity to generate both neuronal cells (including mature neurons), and glial cells (including astrocytes and oligodendrocytes). Scientists at Geron Corporation have also discovered that culturing pPS cells or embryoid body cells in the presence of a hepatocyte differentiation agent promotes enrichment for hepatocyte-like cells. The growth environment may contain a hepatocyte supportive extracellular matrix, such as collagen or Matrigel®. Suitable differentiation agents include various isomers of butyrate and their analogs, exemplified by n-butyrate. The cultured cells are optionally cultured simultaneously or sequentially with a hepatocyte maturation factor, such as an organic solvent like dimethyl sulfoxide, or a cytokine or hormone that promotes cell growth.

pPS-derived differentiated cells are of interest for research, diagnostic, and therapeutic purposes, and can be used to study the genomics of differentiation.

The examples that follow are provided by way of further illustration, and are not meant to imply any limitation to practice of the claimed invention.

EXAMPLES

Example 1: Feeder-free passage of hES cells

Undifferentiated hES cells that had been maintained on primary mouse embryonic feeder cells were harvested, and then maintained in the absence of feeders. The culture wells were coated with Matrigel®, and the cells were cultured in the presence of conditioned nutrient medium obtained from a culture of irradiated primary fibroblasts.

Preparation of conditioned media (CM) from primary mouse embryonic fibroblasts (mEF):

Fibroblasts were harvested from T150 flasks by washing one time with $Ca^{++}/Mg^{++}$ free PBS and incubating in 1.5–2 mL trypsin/EDTA (Gibco) for about 5 min. After the fibroblasts detached from the flask, they were collected in mEF media (DMEM+10% FBS). The cells were irradiated at 4000 rad (508 sec at 140 kV: shelf setting 6 in a Torrex generator), counted and seeded at about 55,000 cells $cm^{-2}$ in mEF media (525,000 cells/well of a 6 well plate). After at least 4 hours, the media were exchanged with SR containing ES media, using 0.3–0.4 mL $cm^{-2}$ of plate surface area. Before addition to the hES cultures, the conditioned medium was supplemented with human bFGF (Gibco). Fibroblast cultures were used in this system for about 1 week, before replacing with newly prepared cells.

Matrigel® coating:

Growth Factor Reduced Matrigel® or regular Matrigel® (Becton-Dickinson, Bedford Mass.) was thawed at 4° C. The Matrigel® was diluted 1:10 to 1:500 (typically 1:30) in cold KO DMEM. 1 mL of solution was added to each 9.6 $cm^2$ well, and incubated at room temp for 1 h. Plates were used within 2 h after coating, or stored at 4° C.

Human ES culture:

Undifferentiated hES colonies were harvested from hES cultures on feeders as follows. Cultures were incubated in ~200 U/mL collagenase IV for about 5 minutes at 37° C. Colonies were harvested by picking individual colonies up with a 20 µL pipet tip under a microscope or scraping and dissociating into small clusters in CM. These cells were then seeded onto Matrigel® in conditioned media at roughly 15 colonies to each 9.6 cm$^2$ well (if 1 colony is ~10,000 cells, then the plating density is ~15,000 cells cm$^{-2}$).

The day after seeding on Matrigel®, hES cells were visible as small colonies (250–2,000 cells) and there were single cells in-between the colonies that appeared to be differentiating or dying. As the hES cells proliferated, the colonies became quite large and very compact, representing the majority of surface area of the culture dish. The hES cells in the colonies had a high nucleus to cytoplasm ratio and had prominent nucleoli, similar to hES cells maintained on feeder cells. At confluence, the differentiated cells in between the colonies represented less than 10% of the cells in the culture.

Six days after seeding, the cultures had become almost confluent. The cultures were split by incubating with 1 mL ~200 U/mL Collagenase IV solution (1 mg/mL in KO DMEM) for ~5 minutes at 37° C. The collagenase solution was aspirated, 2 mL hES medium was added per well, and the hES cells were scraped from the dish with a pipette. The cell suspension was gently triturated to dissociate the cells into small clusters of 10–200 cells. The cells were then re-seeded on Matrigel® coated plates in CM, as above. Cells were seeded at a 1:3 or 1:6 ratio, approximately 90,000 to 170,000 cells cm$^{-2}$, making up the volume in each well to ~3–4 mL. Medium was changed daily, and the cells were split and passaged again at 13 and again at 19 d after initial seeding, or when the culture was near confluency.

On day 19 after initial seeding, cells were harvested and evaluated for surface marker expression by immunofluorescence cell cytometry, using labeled antibodies specific for cell surface markers. The results from this experiment are as follows:

TABLE 1

Phenotype of hPS Cells Grown in the Absence of Feeder Cells

| Marker | Specificity | Percentage of Cells Staining |
| --- | --- | --- |
| SSEA-4 | undifferentiated cells | 92% |
| Tra-1-60 | undifferentiated cells | 92% |
| Tra-1-81 | undifferentiated cells | 83% |
| SSEA-1 | differentiated cells | 12% |

For the hES cells maintained in the absence of feeders, a high percentage express SSEA-4, Tra-1-60 or Tra-1-81. These 3 markers are expressed on undifferentiated human ES cells that are maintained on feeders (Thomson et al., 1998). In addition, there is very little expression of SSEA-1, a glycolipid that is not expressed (or expressed at low levels) on undifferentiated ES cells. Immunohistochemical evaluation of SSEA-4, Tra-1-60 and Tra-1-81 indicates that the expression of these markers in localized to the ES colonies, not the differentiated cells in between the colonies.

Cultures of hES cells have been grown in the absence of feeder cells for over 147 days after initial seeding, with no apparent change in the proliferative capacity or phenotype. Human ES cells maintained on Matrigel® in mEF conditioned medium have a doubling time of about 31–33 hours, similar to the proliferation rate for hES cells grown on mEF feeder cells. H1 cells after 64 days of feeder-free culture showed a normal karyotype.

Example 2: Matrigel® and laminin support feeder-free growth of hES

The growth of the hES cells was followed on different matrix components in medium conditioned using primary mouse embryonic fibroblasts (mEF).

hES cultures were initially harvested from feeder cell cultures maintained in ES medium (80% knockout DMEM (Gibco BRL, Rockville, Md.), 20% knockout serum replacement (Gibco BRL, Rockville, Md.), 1% Non-essential amino acids (Gibco BRL, Rockville, Md.), 1 mM L-glutamine (Gibco), 0.1 mM β-mercaptoethanol (Sigma, St. Louis, Mo.), supplemented with 4 ng/mL recombinant human basic fibroblast growth factor (hbFGF; Gibco)). Cultures were passaged by incubation in ~200 U/mL collagenase IV for about 5–10 minutes at 37° C. Colonies are then harvested by removing individual colonies up with a Pipetman™ under a microscope or scraping, followed by gentle dissociation into small clusters in conditioned medium and then seeded onto matrix coated plates. Cells were seeded at a 1:3 or 1:6 ratio, approximately 90,000 to 170,000 cells cm$^{-2}$). Seeding dilution experiments indicated that the optimal minimum seeding density under these conditions is about 20,000 cells cm$^{-2}$.

Harvested hES cells were seeded onto Matrigel® or gelatin in mEF conditioned medium. The day after seeding, cells plated onto Matrigel® attached to the plate and formed small colonies that were less compact than hES colonies on feeder layers. Over the next few days, the colonies increased in size and the cells became more compact. The resulting culture contained very dense undifferentiated colonies surrounded by differentiated cells.

About one week after seeding the cultures became confluent and could be passaged. In contrast, cells seeded onto gelatin showed poor survival and the cells that survived appeared differentiated. Three hES cell lines, H1, H7 and H9 were cultured on Matrigel® in mEF conditioned medium. Cultures maintained under these conditions for over 180 days continued to display ES-like morphology.

The major components of Matrigel® are laminin, collagen IV and heparin sulfate proteoglycan. The ability of these components to support hES cell culture was tested separately. Laminin, collagen IV or fibronectin (all from Sigma) were diluted to a final concentration of 20 µg/mL, 10 µg/mL and 5 µg/mL in PBS, respectively.

The hES cells seeded onto laminin, fibronectin or collagen IV had colonies of undifferentiated hES cells, although the cultures on fibronectin or collagen IV did not contain as many undifferentiated colonies as the cultures on Matrigel® or laminin. When cells on Matrigel® or laminin reached confluence, the cells within the colonies became very compact, were morphologically very similar to the cells maintained on feeders and were serially passaged. After 40 days (6 passages), cells on Matrigel® and laminin contained a high proportion of colonies which continued to display ES-like morphology in long term culture. However, cells maintained on fibronectin or collagen IV had fewer colonies that displayed appropriate ES-morphology. As controls, cells cultured on Matrigel® or laminin in non-conditioned medium appeared to be proliferating more slowly and showed a differentiated morphology after a few passages.

FIG. 1 shows the morphology of hES cells in feeder-free culture. Panel A (Left Side) shows morphology of hES cells of the H1 line cultured on feeder cells in non-conditioned medium (mEF/RM), or on Matrigel®, laminin, fibronectin, or collagen IV in mEF conditioned medium. Panel B shows morphology of hES cells of the H9 line maintained on Matrigel® in various types of conditioned medium, described in Example 6.

Laminins are major components of all basal laminae in vertebrates, which interact with integrin heterodimers, such as α1β1, α2β1, α3β1, α6β1 and α6β4, on cell surface and mediate cell growth and migration during development. Among these integrins, α6β1 and α6β4 are specific for laminins; other integrins also interact with other matrices. Another experiment tested whether laminin receptors are expressed on hES cells and whether culturing hES on laminin or Matrigel® changes the expression of laminin receptors expression. Expression of integrins including α1, α2, α3, α6, β1 and β4 were examined by FACS analysis on cells maintained on feeders, or on Matrigel® or laminin in conditioned medium. For analyzing integrin expression, cells were stained with a panel of integrin specific antibodies by the laminin-specific integrins investigator kit (Chemicon International, Inc., Temecula, Calif.) and analyzed by FACS as described below.

FIG. 1 Panel C shows integrin expression measured in H1 hES cells maintained on feeders in non-conditioned medium (mEF/RM) or on Matrigel®, or on laminin in mEF conditioned medium (CM).

Cells maintained in Matrigel®/conditioned medium and laminin/conditioned medium were cryopreserved as follows: The cells were frozen in standard hES medium (not conditioned medium) supplemented with 10% DMSO and additional 10% SR (total 30%). The cells were thawed onto Matrigel® or laminin in conditioned medium. Cells maintained normal karyotype after being thawed.

Human ES cells maintained on Matrigel® in mEF conditioned medium showed a doubling time of about 31–33 hours, similar to the proliferation rate for hES cells grown on mEF feeder cells. H1 cells after 64 days of feeder-free culture showed a normal karyotype.

Example 3: Phenotypic markers of hES cells in feeder-free culture

Undifferentiated hES cells may express SSEA-4, Tra-1-60, Tra-1-81, Oct-4, and hTERT under certain conditions. The expression of these markers (if present) typically decreases upon differentiation. In order to assess whether the cells maintained in feeder-free conditions retained these markers, cells were evaluated by immunostaining, reverse transcriptase PCR amplification, and assay for telomerase activity.

FIG. 2 shows surface marker expression in feeder-free cells by FACS analysis. Panel A: Expression of SSEA-4 in H1 cells maintained on feeders in non-conditioned medium (mEF/RM), on Matrigel®, laminin, fibronectin and collagen IV in mEF conditioned medium. Isotype controls are indicated by the dotted lines. Panel B: Mean fluorescence intensity of SSEA-1, SSEA-4, Tra-1-60 and Tra-1-81 in H1 cells cultured on different matrices. Panel C: Mean fluorescence intensity of SSEA-1, SSEA-4, Tra-1-60 and Tra-1-81 in H9 cells cultured on Matrigel® in conditioned medium from different cell lines.

For analysis by fluorescence-activated cell sorting (FACS), the hES cells were dissociated in 0.5 mM EDTA in PBS and resuspended to about 5×10$^5$ cells in 50 µL diluent containing 0.1% BSA in PBS. For analyzing surface marker expression, cells were incubated in the primary antibodies, including IgG isotype control (0.5 µg/test), IgM isotype control (1:10), SSEA-1 (1:10), SSEA-4 (1:20), Tra-1-60 (1:40) and Tra-1-81 (1:80), diluted in the diluent at 4° C. for 30 min. After washing with the diluent, cells were incubated with rat anti-mouse kappa chain antibodies conjugated with PE (Becton Dickinson, San Jose, Calif.) at 4° C. for 30 min. Cells were washed and analyzed on FACSCalibur™ Flow Cytometer (Becton Dickinson, San Jose, Calif.) using CellQuest™ software.

Similar to the hES cells on feeders, cells on Matrigel®, laminin, fibronectin or collagen IV expressed SSEA-4, Tra-1-60 and Tra-1-81. There was very little expression of SSEA-1, a glycolipid that is not expressed by undifferentiated hES cells.

FIG. 3 shows marker expression detected by histochemistry. For analysis by immunocytochemistry, cells were incubated with primary antibodies, including SSEA-1 (1:10), SSEA-4 (1:20), Tra-1-60 (1:40) and Tra-1-81 (1:80), diluted in knockout DMEM at 37° C. for 30 min. Cells were then washed with warm knockout DMEM and fixed in 2% paraformaldehyde for 15 min. After washing with PBS, cells were incubated with 5% goat serum in PBS at RT for 30 min, followed by incubation with the FITC-conjugated goat anti-mouse antibodies (1: 125) (Sigma) at RT for 30 min. Cells were washed, stained with DAPI and mounted. The staining was typically performed ~2 days after passaging. Cells were also examined for expression of alkaline phosphatase, a marker for undifferentiated ES cells. This was performed by culturing the cells on chamber slides, fixing with 4% paraformaldehyde for 15 min, and then washing with PBS. Cells were then incubated with alkaline phosphatase substrate (Vector Laboratories, Inc., Burlingame, Calif.) at room temperature in the dark for 1 h. Slides were rinsed for 2–5 min in 100% ethanol before mounting.

The results show that SSEA-4, Tra-1-60, Tra-1-81, and alkaline phosphatase were expressed by the hES colonies on Matrigel® or laminin, as seen for the cells on feeders—but not by the differentiated cells in between the colonies.

FIG. 4 shows Oct-4 and hTERT expression of H1 cells on feeders and off feeders, as detected by reverse-transcriptase PCR amplification. For radioactive relative quantification of individual gene products, QuantumRNA™ Alternate18S Internal Standard primers (Ambion, Austin Tex., U.S.A.) were employed according to the manufacturer's instructions. Primers and amplification conditions for particular markers are provided in International patent application PCT/US01/01030.

Briefly, the linear range of amplification of a particular primer pair was determined, then coamplified with the appropriate mixture of alternate 18S primers:competimers to yield PCR products with coinciding linear ranges. Before addition of AmpliTaq™ (Roche) to PCR reactions, the enzyme was pre-incubated with the TaqStart™ antibody (ProMega) according to manufacturer's instructions. Radioactive PCR reactions were analyzed on 5% non-denaturing polyacrylamide gels, dried, and exposed to phosphoimage screens (Molecular Dynamics) for 1 hour. Screens were scanned with a Molecular Dynamics Storm 860 and band intensities were quantified using ImageQuant™ software. Results are expressed as the ratio of radioactivity incorporated into the hTERT or Oct-4 band, standardized to the radioactivity incorporated into the 18s band.

The transcription factor Oct-4 is normally expressed in the undifferentiated hES cells and is down-regulated upon differentiation. It was found that the cells maintained on Matrigel® or laminin in conditioned medium (CM) for 21 days express Oct-4, whereas cells maintained in Matrigel® in unconditioned regular medium (RM) did not. Cells maintained on fibronectin or collagen IV, which showed a large degree of differentiation, expressed lower levels of Oct-4 compared to cells on feeders, Matrigel® or laminin.

hTERT and Oct-4 expression was seen in all the culture conditions except Matrigel® and regular medium. Furthermore, after exposure of cells to retinoic acid (RA) or dimethyl sulfoxide (DMSO), factors that promote cell differentiation, the expression of hTERT was markedly decreased.

Pluripotency of the undifferentiated cells cultured without feeders was determined by forming embryoid bodies in suspension culture for 4 days, and then culturing on poly-ornithine coated plates for 7 days. Immunocytochemistry showed staining patterns consistent with cells of the neuron and cardiomyocyte lineages, and cells staining for α-fetoprotein, a marker of endoderm lineage. The undifferentiated cells were also tested for their ability to form teratomas by intramuscular injection into SCID mice. Resulting tumors were excised after 78–84 days. Cell types from all three germ layers were identified by histological analysis.

Example 4: Preparation of immortalized mouse feeder cell lines

Primary mouse embryonic fibroblasts (Robertson, supra) can be immortalized by genetically altering them to express human telomerase reverse transcriptase (hTERT). The fibroblasts (mEF) are infected with a retroviral construct pBABE puro hTERT, containing the hTERT coding sequence driven by the MoLV LTR and the puromycin-resistance gene driven by the SV40 early promoter. Isolates of primary mEFs are cultured in growth medium containing 10% fetal calf serum (HyClone), 2 mM glutamine (Gibco/BRL), and 90% high glucose DMEM (Gibco/BRL). mEFs are split every 3 days at a ratio of 1:2.

After 4 such splits, $5 \times 10^5$ mEFs are plated onto a 100 mM dish. On the next day, cells are infected by replacing the growth medium with a mixture containing 5 mL of retroviral stock ($1 \times 10^6$ pfu/mL) and 4 $\mu$g/mL polybrene, and incubating at 37° C. After 8 h, an additional 5 mL of the retrovirus/polybrene mixture is added and the cells are incubated at 37° C., On the next day, the retrovirus/polybrene mixture is removed and replaced with fresh growth medium. After 4 hr, the mEFs are removed from the plate with 0.5% trypsin/500 mM EDTA (Gibco/BRL) and replated into 2 T150 flasks in 25 mL growth medium/flask. On the next day, the medium is replaced with growth medium supplemented with 0.5 micrograms/mL puromycin.

Cells are split once a week at a ratio of 1:4 for 8 weeks and maintained in puromycin-containing medium. After 8 weeks, cells are trypsinized and replated at a density of 2,000 cells per 150 mm plate. Individual colonies are isolated with cloning cylinders 26 days later, expanded, and screened for telomerase activity.

Example 5: Preparation of the mouse feeder cell line NH190

A permanent mouse cell line was established that is suitable for conditioning medium for the culture of primate pluripotent stem (pPS) cells. The NHG190 line is a mouse embryonic fibroblast cell line immortalized with telomerase that is triple drug resistant, and expresses green fluorescent protein (GFP).

Two mouse strains were obtained from Jackson Laboratory (Bar Harbor, Ma.) that have a transgene for resistance to the antibiotics neomycin or hygromycin. The C57BL/6J TgN(pPGKneobpA)3Ems mice and C57BL/6J-TgN (pPWL512hyg)1Ems mice from Jackson Labs were crossbred. Embryos that were both neomycin- and hygromycin-resistant were dissected at day 13.5 post conception according to standard protocols for preparing mouse embryonic fibroblasts (mEF) for feeder layers (E. J. Robertson, pp. 71–112 in *Teratocarcinoma and Embryonic Stem Cell Lines*, ed. E. J. Robertson, Oxford: IRL Press, 1987). The derived mEF cells were stored frozen.

The mEFs were thawed in growth medium containing 20% fetal calf serum (HyClone), 2 mM L-glutamine (Gibco/BRL), 80% DMEM (Gibco/BRL). The cells were expanded using 1:2 split ratios for 4 passages. Two flasks that had reached ~75% confluency were fed with fresh medium 4 h before electroporation. Cells were removed from the flasks with 0.5% trypsin/500 mM EDTA (Gibco/BRL), pelleted at 400×g for 5 min at room temperature, and resuspended in the growth medium at a concentration of $4 \times 10^6$ cells/mL.

The cell suspension was divided into two 500 $\mu$L aliquots and transferred to two 0.4 cm gap electroporation cuvettes (BioRad). One cuvette received 5 $\mu$g of the control plasmid (pBS212; puromycin-resistance gene driven by the SV40 early enhancer/promoter); the other received 5 micrograms of pGRN190, comprising the murine telomerase reverse transcriptase (mTERT) coding region driven by MPSV promoter plus puromycin resistance gene driven by the SV40 early enhancer/promoter. The cells and DNA were mixed by hand, and electroporated using a BioRad gene Pulser with a BioRad capacitance extender at a setting of 300V, 960 $\mu$F.

Each aliquot of cells was transferred to an individual 150 cm plate containing 25 mL of growth medium. The medium on the plates was exchanged on the following day, and on the next day, growth medium was replaced by growth medium plus 0.5 $\mu$g/mL puromycin. The medium on the plates was exchanged for fresh puromycin-containing medium every 48 hrs until 29 days after electroporation. At this time, large individual colonies of puromycin-resistant cells were evident in both the pBS212- and pGRN190- electroporated plates. Ten colonies from the control plate and 12 from the pGRN190-electroporated plate were isolated with cloning cylinders and each colony was transferred to 1 well of a 48-well plate (1 well per colony).

One week later, all surviving colonies that had expanded to reach confluence in the 48 well plate (three control colonies, 1 pGRN190-electroporated colony) were transferred individually to wells of a 24 well plate. Six days later, the only colony that had continued to expand was derived from the pGRN190-electroporated plate, and was subsequently designated NH190. The cells were maintained in growth medium plus 0.5 $\mu$g/mL puromycin.

To facilitate monitoring of the cells in mixed culture populations and in vivo, NH190 cells were further infected with a retroviral construct conferring expression of green fluorescent protein (GFP). The enhanced GFP sequence from plasmid pEGFP-1 is one of the Living Colors™ fluorescent protein vectors, available from ClonTech. It contains an enhanced GFP encoding region, with changes that alter restriction nuclease cleavage sites, and shift the excitation and emission wavelengths of the encoded protein. The EGFP-1 sequence was cloned into the vector pMSCV.neo, ClonTech cat # K1062-1. NH190 cells were transduced with the engineered vector, and GFP positive cells were separated by FACS sorting. The GFP expressing cell line was designated NHG190. These cells have been carried in culture for over 3 months.

Example 6: Use of conditioned medium from immortalized mouse cells to support feeder-free culture of human ES cells Conditioned medium from several cell lines were tested for their ability to support the growth of human embryonic stem cells in feeder-free cultures. The media tested were from mEF (primary mouse embryonic fibroblasts), STO (immortal mouse embryonic fibroblast cell line), NHG190 (Example 5), BJ (human foreskin fibroblast cell line immortalized with telomerase), and RPE (human retinal epithelial cell line immortalized with telomerase).

Medium used for growing cells was as follows. 1. mEF medium: 90% DMEM (Gibco BRL, Rockville, Md.), 10% fetal bovine serum (FBS) (heat inactivated) (Hyclone), and 2 mM L-glutamine. 2. STO medium: mEF medium supplemented with 0.1 mM non-essential amino acids. 3.BJ 5ta medium: 90% DMEM and 10% Cosmic calf serum (not heat inactivated). 3. NHG190 medium: mEF medium supplemented with additional 10% FBS. 4. RPE medium: 90% DMEM/F12, 10% FBS (not heat inactivated), 10 ml L-glutamine and 3.48 g/Lsodium bicarbonate. 5. Differentiation medium: 80% knockout Dulbecco's modified Eagle's medium (KO DMEM), 1 mM L-glutamine, 0.1 mM β-mercaptoethanol and 1% nonessential amino acids, supplemented with 20% FBS.

To prepare conditioned medium, the respective cell lines were harvested by washing once with $Ca^{++}/Mg^{++}$ free PBS, incubating in trypsin/EDTA (Gibco) for about 5 min, and suspending in mEF medium. The cells were irradiated at ~4000 rad (~508 sec at 140 kV: shelf setting 6 in a Torrex generator, EG&G Astrophysics Research Corp., Long Beach Calif.). They were then counted, and seeded at ~55,000 cells/cm$^2$ for mEFs, ~38,000/cm$^2$ for NHG190 cells, ~95,000/Cm$^2$ for STO cells, ~80,000/cm$^2$ for BJ cells, ~90,000/cm$^2$ for RPE cells. After at least 4 h, the medium was exchanged with ES medium. Conditioned medium was collected daily thereafter, and used for feeding of hES cultures. Before addition to the hES cultures, each conditioned medium was supplemented with 4 ng/mL of human basic fibroblast growth factor (hbFGF; Gibco).

FIG. 1, Panel B (Right Side) shows morphology of hES cells of the H9 line maintained on Matrigel® in medium conditioned by mEF, NHG190, STO and BJ, compared with unconditioned regular medium (RM). The cells in RPE conditioned medium differentiated within the first week of culture. The cells in the other conditioned mediums all had hES colonies with appropriate ES-morphology. Based on the morphology, confluence of the culture, and the ratio of differentiated to undifferentiated cells the conditioned medium can be ranked in order of decreasing preference as follows: primary mEF, NHG190, STO, and BJ.

Similar to cells maintained in conditioned medium from primary mEF, cells on Matrigel® or laminin in medium conditioned by other cell lines, including NHG190, STO and BJ, expressed high levels of SSEA-4, Tra-1-60 and Tra-1-81 but low levels of SSEA-1 as analyzed by FACS analysis (FIG. 2C). Cells on Matrigel® or laminin in mEF conditioned medium or NHG190 conditioned medium were able to differentiate into three germ layer cell types. Immunocytochemical analysis of the differentiated cultures showed positive staining for β-tubulin III consistent with neurons (ectoderm lineage), cardiac troponin I consistent with cardiomyocytes (mesoderm lineage), and α-fetoprotein, consistent with cells of the endoderm lineage.

In Examples 1 and 2, medium was prepared by adding 4 ng/mL hbFGF to the medium before conditioning with the mEFs, and then again when the conditioned medium was collected and used for feeding of the hES cells. To determine if both additions of hbFGF to the medium are necessary to maintain the ES cells in the undifferentiated state, experiments were performed in which one or both additions of hbFGF were eliminated.

Cultures maintained in conditioned medium without the second addition of hbFGF did not appear healthy at early passages, and appeared differentiated after 29 days in culture. Cells maintained in conditioned medium without the first addition of hbFGF displayed mostly differentiated morphology, but still formed smaller undifferentiated colonies after 27 days in culture. Cells maintained in conditioned medium without either addition of hbFGF completely differentiated after 18 days. In contrast, cells cultured in conditioned medium prepared with both additions of bFGF appeared healthy and undifferentiated in long-term culture.

Thus, preparing conditioned medium by adding bFGF both before and after culturing with the feeder cells helps prevent differentiation of hPS cells in the subsequent feeder-free culture.

Storage of conditioned medium was tested as follows: Batch medium was prepared by conditioning for 1–2 days in mEF cell cultures as described, and stored at 4° C. in sealed culture flasks. Feeder-free hES cell cultures were maintained with stored medium exchanged daily. Characteristic morphological features of undifferentiated stem cells were still present after at least 7 days, comparable to hES cells maintained in freshly conditioned medium.

To determine if leukemia inhibitory factor (LIF) can substitute for conditioned medium in maintaining hES cells without feeders, cells of the H1 and H9 line were cultured on Matrigel® in ES medium containing LIF at a final concentration of 1500, 1,000, or 500 U/mL (recombinant LIF from R&D systems; Catalog # 250-L). Cells were simultaneously cultured in mEF conditioned medium as the positive control, and unconditioned ES medium as negative control. After one week, cultures in medium either with or without LIF showed a large degree of differentiation, while cultures maintained in mEF conditioned medium contained predominately undifferentiated colonies. These data indicate that LIF alone will not maintain hES cells in an undifferentiated state in the absence of feeders.

Example 7: Preparation of human feeder cell lines

Cells were derived from hES cells that have the morphological criteria of fibroblasts or mesenchymal cells. They are capable of supporting hES cells in feeder-free culture.

The H9 hES cell line was obtained as described elsewhere in this disclosure. To form embryoid bodies, the hES cells were harvested after incubation with ~200 U/mL collagenase IV at 37° C. for 10 min, and dissociated into small clusters in differentiation media and cultured in non-adherent cell culture plates (Costar) to form aggregates in suspension. ~2×10$^6$ cells were seeded into each well (9.6 cm$^2$). After 2 days in suspension, the aggregates were transferred into gelatin-coated plates. They attached to the plates and continued to differentiate into cells with different morphologies. Fibroblast-like cells were observed in clusters of 100–1000 cells in the mixed population of the differentiated cells after an additional 11 days.

To isolate fibroblast-like cells, the culture was incubated in ~200 U/mL collagenase IV for 3 min at 37° C. These clusters of fibroblast-like cells were removed with a Pipetman™ under a microscope and either transferred directly to a tube containing the differentiation media or released into the collagenase solution, and subsequently collected. The cells were spun, resuspended in differentiation media and plated onto one well of 6-well plate. The cells proliferated, and were serially passaged. The cultures were switched to mEF media in the third passage. In all procedures, cells were fed every 2–3 days.

To introduce telomerase into the fibroblast-like cells, they were infected with retrovirus expressing hTERT as follows. Cells were seeded onto 6-well plates at 8.6×10$^4$ cells/well (9.6 cm$^2$) one day before infection, incubated with virus-containing media supplemented with 4 µg/mL polybrene for 8 h before changed to mEF medium. Different wells were infected with pBABE-hTERT or a pBABE vector control.

The cells were cultured for additional 6 days, and selected in puromycin at a final concentration of 1.6 µg/mL for an additional 8 days. The cells were then harvested and re-seeded in mEF medium.

The cells were expanded and continued to display fibroblast-like morphology for 50 days. Cells were collected for TRAP assay 20 days after the infection. The cells were maintained in mEF medium from day 0 to 27 and were switched to differentiation media from day 28 to day 43. Cells were counted at each passage after the selection and the population doubling was calculated.

FIG. 5 (Panel A) shows the morphology of the derived hEF-like cell line, after transduction with retrovirus pBABE containing an hTERT expression cassette. Panel B (below) shows the growth curves of the hEF-like cells transduced for hTERT expression (pBABE-hTERT=telomerized cells; pBABE (alone)=vector control). Both cell lines proliferate in culture for at least 8 doublings, presumably because they are derived from embryonic cells and have not yet reached the Hayflick limit.

Telomerase activity of hEF cells was analyzed by TRAP assay (Kim et al., Nucleic Acids Res. 25:2595, 1997). Cells transduced with the hTERT expression cassette showed positive telomerase activity, whereas the control cells did not show any telomerase activity. The hTERT-hEF cells serially passaged with a similar proliferation rate as that of the control cells.

Example 8: Harvesting conditioned medium from human feeder cells

The hTERT-expressing human fibroblast-like cells prepared according to the previous example were harvested by washing once with $Ca^{++}/Mg^{++}$ free PBS and incubating in 1.5–2 mL trypsin/EDTA (Gibco) for about 2 min. After the cells detached from the plate, they were collected in mEF medium. The cells were irradiated at 4000 rad, counted and seeded at about $3.7-5\times10^5$ cells/well. After at least 16 h, the medium was exchanged with hES media+4 ng/mL hbFGF (serum replacement medium described above, with 4 ng/mL exogenously added human basic fibroblast growth factor). Three to four mL were used per well of a 6 well plate.

Conditioned medium was collected daily for feeding of hES cultures. Before addition to the hES cultures, this conditioned medium was supplemented with 4 ng/mL of hbFGF (Gibco). The hTERT-hEF cultures were used in this system for 1–2 weeks.

Example 9: Use of conditioned medium from differentiated human cells to support feeder-free culture of human stem cells The hTERT-transduced hEF cells were tested for their ability to support hES growth as follows. The H1 hES cell line maintained on Matrigel® in medium conditioned using primary mouse embryonic fibroblasts was dissociated and resuspended in medium conditioned by the human fibroblast-like cells.

FIG. 6 shows hES maintained in hEF conditioned medium. Cultures of hES cells replated in feeder-free culture on Matrigel® supported by hEF conditioned medium (Panels C & F), formed colonies with morphology characteristic of undifferentiated hES cells. The cultures appeared indistinguishable from hES cells grown directly on a layer of primary mEF feeder cells (Panels A & D) or on Matrigel® in medium conditioned by primary mEF. In each of these conditions, healthy colonies of hES cells increased in size, and had characteristic features of undifferentiated embryonic stem cells (Panels A, B, & C). A few colonies showed a degree of differentiation (Panels D, E, & F), but the extent of differentiation was similar under each of the culture conditions.

Seven days after the seeding, the cultures had become almost confluent and were split by incubating in ~200 U/mL collagenase IV for about 5 minutes at 37° C. and scraping the dish with a pipette. The cell suspension was transferred to a 15-mL conical tube and gently triturated to dissociate the cells into small clusters of about 10–500 cells. The cells were then re-seeded onto Matrigel®-coated plates in CM. Cells were seeded at a 1:3 or 1:4 ratio, 130,000 to 170,00 cells $cm^{-2}$. Cells have been maintained under this condition for over 30 days while displaying morphology characteristic of hES cells.

Example 10: Medium conditioned by hEFs from the H1 line

A second line of medium-conditioning cells was developed from a different hES cell line designated H1. Embryoid bodies were formed as before, and after 4 days in suspension culture were plated onto gelatin-coated plates for an additional 9 days.

In this example, the cell population was developed from bulk culture rather than being selected out by pipette. The cultures were incubated in 2 mg/mL Collagenase type II in PBS for 30 min at 37° C. The cells were harvested, dissociated, centrifuged, resuspended in differentiation medium, and plated in a 6-well plate. The proliferating cells were passaged in hEF medium (90% DMEM, 10% heat-inactivated FBS, 0.1 mM non-essential amino acids, and 2 mM L-glutamine), and fed every 2–3 days. After two passages, the cell population appeared homogeneous with morphological characteristics of fibroblasts. This cell line was designated HEF1.

Subpopulations were transduced with the retrovirus telomerase expression vector (pBABE-hTERT), or with vector control, as in Example 7.

FIG. 7 (Panel A) shows the morphology of the HEF1 cell line. Panel B (below) shows telomerase activity, as measured in the TRAP assay. Cells transduced with the hTERT expression cassette showed positive telomerase activity at 20 or 65 days after transduction. The untransduced cell line, or cells transduced with the vector control showed no telomerase activity.

FIG. 8 shows the growth curves of the hTERT-transduced HEF1 cells, and cells transduced with vector control. Both lines doubled about once every 2 days, until the 38 day point, when the control cells stopped dividing (presumably because they had reached the Hayflick limit). The hTERT-transfected cells continued proliferating beyond the 60 day point (30 doublings) at a consistent growth rate.

FIG. 9 is a micrograph of the hTERT transduced cells and control cells, after staining for senescence-associated β-galactosidase, a known biomarker for cellular aging (Dimitri et al., Proc. Natl. Acad. Sci. U.S.A. 92:9363, 1995). Cells grown on chamber slides were fixed 2 min in 0.2% glutaraldehyde in PBS, washed with PBS, and incubated overnight in 1 mg/mL 5-bromo-4-chloro-3-indolyl-D-galactosidase (X-gal), 5 mM $K_4Fe(CN)_6$, 5 mM $K_3Fe(CN)_6$, 150 mM NaCl, 2 mL $MgCl_2$, in 40 mM citric acid phosphate buffer pH 6.0. The HEF1 control cells stained heavily for β-galactosidase, whereas the hTERT transduced cells did not. The combined results indicate that the expression of hTERT extends the life-span characteristics of the HEF1 cells.

Medium was conditioned as in Example 8, using HEF1 cells irradiated at 6000 rad, and seeded at ~4.1 to $5.5\times10^4$ cells $cm^{-2}$. The medium was tested for its ability to support growth of the H9 hES cell line cultured on a Matrigel® substrate.

FIG. 10 shows colonies of hES cells after passaging into medium conditioned either by mouse embryonic fibroblasts, or by the HEF1 cell line. The hES cells have been maintained using the HEF1 conditioned medium for 4 passages, continuing to display the morphology of undifferentiated ES cells. The hES cells were found to maintain expression of hTERT and Oct-4. As shown in Panel B, they also continued to demonstrate telomerase activity, as measured in the TRAP assay, which is characteristic of undifferentiated hES cells.

It is understood that certain adaptations of the invention described in this disclosure are a matter of routine optimization for those skilled in the art, and can be implemented without departing from the spirit of the invention, or the scope of the appended claims.

What is claimed as the invention is:

1. A method for proliferating human blastocyst-derived pluripotent stem cells in a substantially undifferentiated form, comprising culturing the stem cells in a growth environment that is essentially free of feeder cells, but that contains an extracellular matrix and a conditioned medium produced by a method comprising:

a) culturing cells in a tissue culture medium, thereby conditioning the medium; and then b) harvesting the conditioned medium from the culture; wherein the cells used to condition the medium are from a non-malignant mouse cell line immortalized by genetic engineering, or a non-malignant human cell line that proliferates in culture for at least 60 days.

2. The method of claim 1, wherein the pluripotent stem cells are a line of human embryonic stem (hES) cells.

3. The method of claim 1, wherein the cell line used to condition the medium is an immortalized mouse cell line.

4. The method of claim 1, wherein the cell line used to condition the medium is a human cell line.

5. The method of claim 1, wherein the cell line used to condition the medium is a mesenchymal cell line.

6. The method of claim 1, wherein the cell line used to condition the medium is a fibroblast line.

7. The method of claim 4, wherein the cell line used to condition the medium has been obtained by differentiating human embryonic stem cells ex vivo.

8. The method of claim 1, wherein the cell line used to condition the medium is euploid.

9. The method of claim 1, wherein the cell line used to condition the medium has been genetically altered to express telomerase reverse transcriptase (TERT) at an elevated level.

10. A method for preparing a conditioned medium for proliferating primate pluripotent stem (pPS) cells, comprising:

a) culturing cells in a tissue culture medium, thereby conditioning the medium; and then b) harvesting the conditioned medium from the culture; wherein the cells used to condition the medium are from a human cell line immortalized with telomerase reverse transcriptase (TERT); and wherein pPS cells proliferate without differentiation when cultured in an environment essentially free of feeder cells but comprising the conditioned medium, an extracellular matrix, and a growth factor.

11. The method of claim 10, further comprising adding a fibroblast growth factor to the medium before or after harvesting.

12. The method of claim 11, wherein the fibroblast growth factor is basic FGF or FGF-4.

13. The method of claim 10, wherein the cells used to condition the medium are irradiated.

14. The method of claim 10, wherein the cells used to condition the medium are mesenchymal cells.

15. The method of claim 10, wherein the cells used to condition the medium are fibroblasts.

16. The method of claim 10, wherein the cell line used to condition the medium has been obtained by differentiating human embryonic stem cells ex vivo.

17. The method of claim 10, wherein the cells used to condition the medium have been genetically altered to express telomerase reverse transcriptase (TERT) at an elevated level.

18. A composition of undifferentiated pluripotent stem cells obtained from a human blastocyst, proliferating in a growth environment containing an extracellular matrix and a medium conditioned by:

a) culturing cells in a tissue culture medium, thereby conditioning the medium; and then b) harvesting the conditioned medium from the culture; wherein the cells used to condition the medium are from a non-malignant mouse cell line immortalized by genetic engineering, or a human cell line that proliferates in culture for at least 60 days.

19. The composition of claim 18, wherein the cells used to condition the medium are an immortalized mouse cell line.

20. The composition of claim 18, wherein the cells used to condition the medium are human cells.

21. The composition of claim 18, wherein the pluripotent stem cells proliferating in the composition are a line of human embryonic stem (hES) cells.

22. The composition of claim 18, wherein the cells used to condition the medium are from a line of human cells that proliferates in culture for at least 60 days.

23. The composition of claim 18, wherein the cells used to condition the medium have been obtained by differentiating a culture of hES cells, and then selecting mesenchymal or fibroblast-like cells from the culture.

24. The composition of claim 18, wherein the cells used to condition the medium have been immortalized.

25. A method for preparing a conditioned medium for proliferating human blastocyst-derived pluripotent stem cells, comprising:

a) culturing cells of a telomerized mammalian cell line in a tissue culture medium, thereby conditioning the medium;

b) harvesting the conditioned medium from the culture; and then c) adding a growth factor to the medium;

wherein pPS cells proliferate without differentiation when cultured in an environment essentially free of feeder cells, but comprising an extracellular matrix and the conditioned medium.

26. The method of claim 25, wherein the cells used to condition the medium are mesenchymal cells.

27. The method of claim 25, wherein the cells used to condition the medium are fibroblasts.

28. The method of claim 25, wherein cells used to condition the medium were obtained by differentiating hES cells ex vivo.

29. The method of claim 25, wherein the cells used to condition the medium have are human.

30. A conditioned medium for proliferating human blastocyst-derived pluripotent stem cells, produced by a method comprising:

a) culturing cells of a telomerized mammalian cell line in a tissue culture medium, thereby conditioning the medium;

b) harvesting the conditioned medium from the culture; and then c) adding a growth factor to the medium;

wherein pPS cells proliferate without differentiation when cultured in an environment essentially free of feeder cells, but comprising an extracellular matrix and the conditioned medium.

31. The conditioned medium of claim 30, wherein the cells used to condition the medium are mesenchymal cells.

32. The conditioned medium of claim 30, wherein the cells used to condition the medium are fibroblasts.

33. The conditioned medium of claim 30, wherein cells used to condition the medium were obtained by differentiating hES cells ex vivo.

34. The conditioned medium of claim 30, wherein the cells used to condition the medium are human.

35. A method for determining whether a non-malignant human cell line is capable of producing conditioned medium according to claim 30, comprising:

a) providing a growth environment essentially free of feeder cells, but containing an extracellular matrix and a medium that has been conditioned by culturing with the human cell line; and b) determining whether pPS cells cultured in the growth environment proliferate without differentiating.

* * * * *